(12) United States Patent
Kusens et al.

(10) Patent No.: US 11,937,915 B2
(45) Date of Patent: Mar. 26, 2024

(54) METHODS AND SYSTEMS FOR DETECTING STROKE SYMPTOMS

(71) Applicant: CERNER INNOVATION, INC., North Kansas City, MO (US)

(72) Inventors: Michael Kusens, Cooper City, FL (US); Neil Kusens, Sherman Oaks, CA (US)

(73) Assignee: Cerner Innovation, Inc., North Kansas City, MO (US)

( * ) Notice: Subject to any disclaimer, the term of this patent is extended or adjusted under 35 U.S.C. 154(b) by 0 days.

(21) Appl. No.: 17/576,593

(22) Filed: Jan. 14, 2022

(65) Prior Publication Data
US 2022/0133174 A1 May 5, 2022

Related U.S. Application Data

(63) Continuation of application No. 16/816,626, filed on Mar. 12, 2020, now Pat. No. 11,241,169, which is a
(Continued)

(51) Int. Cl.
*A61B 5/11* (2006.01)
*A61B 5/00* (2006.01)
(Continued)

(52) U.S. Cl.
CPC .............. *A61B 5/11* (2013.01); *A61B 5/0077* (2013.01); *A61B 5/1176* (2013.01);
(Continued)

(58) Field of Classification Search
CPC ....... A61B 5/11; A61B 5/0077; A61B 5/1176; A61B 5/4064; A61B 5/746; G06T 7/0012;
(Continued)

(56) References Cited

U.S. PATENT DOCUMENTS

| 4,669,263 A | 6/1987 | Sugiyama |
| 4,857,716 A | 8/1989 | Gombrich et al. |

(Continued)

FOREIGN PATENT DOCUMENTS

| AU | 2014308590 A1 * | 3/2016 | ........... A61B 3/0025 |
| CN | 101938953 A * | 1/2011 | ............... A61F 2/12 |

(Continued)

OTHER PUBLICATIONS

US 9,948,899 B1, 04/2018, Kusens (withdrawn)
(Continued)

*Primary Examiner* — Dramos Kalapodas
(74) *Attorney, Agent, or Firm* — Kilpatrick Townsend & Stockton LLP

(57) ABSTRACT

A stroke detection system analyzes images of a person's face over time to detect asymmetric changes in the position of certain reference points that are consistent with sagging or drooping that may be symptomatic of a stroke or TIA. On detecting possible symptoms of a stroke or TIA, the system may alert caregivers or others, and log the event in a database. Identifying stroke symptoms automatically may enable more rapid intervention, and identifying TIA symptoms may enable diagnostic and preventative care to reduce the risk of a future stroke.

19 Claims, 13 Drawing Sheets

Related U.S. Application Data continuation of application No. 15/395,762, filed on Dec. 30, 2016, now Pat. No. 10,614,288.

(60) Provisional application No. 62/273,735, filed on Dec. 31, 2015.

(51) Int. Cl.

| | | |
|---|---|---|
| *A61B 5/1171* | (2016.01) | |
| *G06F 18/22* | (2023.01) | |
| *G06T 7/00* | (2017.01) | |
| *G06T 7/20* | (2017.01) | |
| *G06T 7/292* | (2017.01) | |
| *G06T 11/60* | (2006.01) | |
| *G06V 20/52* | (2022.01) | |
| *G06V 20/64* | (2022.01) | |
| *G06V 40/16* | (2022.01) | |
| *G06V 40/20* | (2022.01) | |
| *G08B 5/22* | (2006.01) | |
| *G08B 13/196* | (2006.01) | |
| *G08B 21/18* | (2006.01) | |
| *G08B 25/00* | (2006.01) | |
| *G16H 10/60* | (2018.01) | |
| *G16H 15/00* | (2018.01) | |
| *G16H 20/10* | (2018.01) | |
| *G16H 30/20* | (2018.01) | |
| *G16H 40/20* | (2018.01) | |
| *G16H 40/63* | (2018.01) | |
| *G16H 40/67* | (2018.01) | |
| *G16H 50/30* | (2018.01) | |
| *G16H 80/00* | (2018.01) | |
| *H04N 7/18* | (2006.01) | |
| *H04N 13/204* | (2018.01) | |
| *H04N 13/207* | (2018.01) | |
| *H04N 23/63* | (2023.01) | |
| *G06F 3/0482* | (2013.01) | |
| *G06F 3/04847* | (2022.01) | |
| *G08B 21/04* | (2006.01) | |
| *H04N 13/00* | (2018.01) | |

(52) U.S. Cl.
CPC ............ *A61B 5/4064* (2013.01); *A61B 5/746* (2013.01); *G06F 18/22* (2023.01); *G06T 7/0012* (2013.01); *G06T 7/0016* (2013.01); *G06T 7/20* (2013.01); *G06T 7/292* (2017.01); *G06T 11/60* (2013.01); *G06V 20/52* (2022.01); *G06V 20/647* (2022.01); *G06V 40/172* (2022.01); *G06V 40/20* (2022.01); *G08B 5/22* (2013.01); *G08B 13/196* (2013.01); *G08B 21/182* (2013.01); *G08B 25/009* (2013.01); *G16H 10/60* (2018.01); *G16H 15/00* (2018.01); *G16H 20/10* (2018.01); *G16H 30/20* (2018.01); *G16H 40/20* (2018.01); *G16H 40/63* (2018.01); *G16H 40/67* (2018.01); *G16H 50/30* (2018.01); *G16H 80/00* (2018.01); *H04N 7/18* (2013.01); *H04N 7/181* (2013.01); *H04N 7/183* (2013.01); *H04N 13/204* (2018.05); *H04N 13/207* (2018.05); *H04N 23/63* (2023.01); *G06F 3/0482* (2013.01); *G06F 3/04847* (2013.01); *G06T 2200/04* (2013.01); *G06T 2200/24* (2013.01); *G06T 2207/10012* (2013.01); *G06T 2207/10021* (2013.01); *G06T 2207/10024* (2013.01); *G06T 2207/20221* (2013.01); *G06T 2207/30201* (2013.01); *G06T 2207/30232* (2013.01); *G06V 40/161* (2022.01); *G08B 13/19639* (2013.01); *G08B 21/0476* (2013.01); *H04N 2013/0085* (2013.01)

(58) Field of Classification Search
CPC . G06T 7/20; G06T 7/292; G06T 11/60; G06T 2200/04; G06T 2200/24; G06T 2207/10012; G06T 2207/10021; G06T 2207/10024; G06T 2207/20221; G06T 2207/30201; G06V 10/44; G06V 20/52; G06V 20/647; G06V 40/172; G06V 40/20; G08B 5/22; G08B 13/196; G08B 21/182; G08B 25/009; G16H 10/60; G16H 30/20; G16H 50/30; G16H 40/67; H04N 7/18; H04N 7/181; H04N 7/183; H04N 13/204

See application file for complete search history.

(56) References Cited

U.S. PATENT DOCUMENTS

| | | |
|---|---|---|
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 * | 3/2009 | Wen .............. G16H 30/40 382/128 |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,190,447 B2 | 5/2012 | Hungerford et al. |
| 8,224,108 B2 | 7/2012 | Steinberg et al. |
| 8,237,558 B2 | 8/2012 | Seyed et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | Mcnair |
| 8,565,500 B2 | 10/2013 | Neff |

(56) References Cited

U.S. PATENT DOCUMENTS

| | | |
|---|---|---|
| 8,620,682 B2 | 12/2013 | Bechtel et al. |
| 8,655,680 B2 | 2/2014 | Bechtel et al. |
| 8,700,423 B2 | 4/2014 | Eaton et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,269,012 B2 | 2/2016 | Fotland |
| 9,292,089 B1 | 3/2016 | Sadek |
| 9,305,191 B2 | 4/2016 | Long et al. |
| 9,367,270 B1 | 6/2016 | Robertson |
| 9,408,561 B2 | 8/2016 | Stone et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 9,934,427 B2 | 4/2018 | Derenne et al. |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,210,378 B2 | 2/2019 | Kusens et al. |
| 10,225,522 B1 | 3/2019 | Kusens |
| 10,342,478 B2 | 7/2019 | Kusens |
| 10,524,722 B2 | 1/2020 | Kusens et al. |
| 10,614,288 B2 | 4/2020 | Kusens et al. |
| 10,643,446 B2 | 5/2020 | Kusens et al. |
| 10,922,936 B2 | 2/2021 | Kusens et al. |
| 10,922,946 B2 | 2/2021 | Kusens et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0108223 A1* | 6/2003 | Prokoski .............. A61B 5/415 382/209 |
| 2003/0135390 A1 | 7/2003 | Obrien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | Delean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Agassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0033072 A1 | 2/2007 | Bildirici |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins et al. |
| 2009/0119843 A1 | 5/2009 | Rodgers et al. |
| 2009/0196510 A1* | 8/2009 | Gokturk .............. G06F 16/53 382/305 |
| 2009/0224924 A1 | 9/2009 | Thorp |
| 2009/0278934 A1 | 11/2009 | Ecker et al. |
| 2009/0322513 A1 | 12/2009 | Hwang et al. |
| 2009/0326340 A1* | 12/2009 | Wang .................. A61B 5/002 600/301 |
| 2010/0117836 A1 | 5/2010 | Seyed et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton et al. |
| 2011/0106561 A1 | 5/2011 | Eaton et al. |
| 2011/0175809 A1 | 7/2011 | Markovic et al. |
| 2011/0190593 A1 | 8/2011 | Mcnair |
| 2011/0227740 A1 | 9/2011 | Wohltjen |
| 2011/0245707 A1 | 10/2011 | Castle et al. |
| 2011/0254682 A1 | 10/2011 | Sigrist |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | Okeefe et al. |
| 2012/0026308 A1 | 2/2012 | Johnson et al. |
| 2012/0075464 A1 | 3/2012 | Derenne et al. |

(56) References Cited

U.S. PATENT DOCUMENTS

| | | |
|---|---|---|
| 2012/0092162 A1 | 4/2012 | Rosenberg |
| 2012/0098918 A1 | 4/2012 | Murphy |
| 2012/0140068 A1 | 6/2012 | Monroe et al. |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0168397 A1 | 6/2014 | Greco et al. |
| 2014/0191861 A1 | 7/2014 | Scherrer |
| 2014/0191946 A1 | 7/2014 | Cho et al. |
| 2014/0213845 A1 | 7/2014 | Bechtel et al. |
| 2014/0267625 A1 | 9/2014 | Clark et al. |
| 2014/0267736 A1 | 9/2014 | Delean |
| 2014/0309789 A1 | 10/2014 | Ricci |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0055085 A1* | 2/2015 | Fonte ............... G02C 7/027 700/98 |
| 2015/0057635 A1 | 2/2015 | Bechtel et al. |
| 2015/0061891 A1 | 3/2015 | Oleson et al. |
| 2015/0109442 A1 | 4/2015 | Derenne et al. |
| 2015/0206415 A1 | 7/2015 | Wegelin et al. |
| 2015/0227680 A1* | 8/2015 | Mainkar ............... G06T 17/00 703/11 |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0098676 A1 | 4/2016 | Kusens et al. |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0285416 A1 | 9/2016 | Tiwari et al. |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0116473 A1 | 4/2017 | Sashida et al. |
| 2017/0143240 A1 | 5/2017 | Stone et al. |
| 2017/0163949 A1 | 6/2017 | Suzuki |
| 2017/0195637 A1 | 7/2017 | Kusens et al. |
| 2017/0214902 A1 | 7/2017 | Braune |
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0116528 A1 | 5/2018 | Tzvieli et al. |
| 2018/0144605 A1 | 5/2018 | Kusens |
| 2018/0189946 A1 | 7/2018 | Kusens et al. |
| 2018/0190098 A1 | 7/2018 | Kusens |
| 2018/0357875 A1 | 12/2018 | Kusens |
| 2019/0006046 A1 | 1/2019 | Kusens et al. |
| 2019/0029528 A1* | 1/2019 | Tzvieli ............... A61B 5/6814 |
| 2019/0043192 A1 | 2/2019 | Kusens et al. |
| 2019/0057592 A1 | 2/2019 | Kusens |
| 2019/0205630 A1 | 7/2019 | Kusens |
| 2019/0206218 A1 | 7/2019 | Kusens et al. |
| 2019/0209022 A1 | 7/2019 | Sobol et al. |
| 2019/0228866 A1 | 7/2019 | Weffers-albu et al. |
| 2019/0307405 A1 | 10/2019 | Terry et al. |
| 2020/0050844 A1 | 2/2020 | Kusens |
| 2020/0210679 A1 | 7/2020 | Kusens et al. |
| 2020/0226905 A1 | 7/2020 | Kusens et al. |
| 2021/0202052 A1 | 7/2021 | Bechtel et al. |
| 2022/0054197 A1* | 2/2022 | Plessers ............... A61B 34/10 |

FOREIGN PATENT DOCUMENTS

| | | |
|---|---|---|
| DE | 19844918 A1 | 4/2000 |
| WO | 2007081629 A2 | 7/2007 |
| WO | 2009018422 A1 | 2/2009 |
| WO | 2012122002 A1 | 9/2012 |
| WO | 2018/218286 A1 | 12/2018 |

OTHER PUBLICATIONS

Camera System is Part of an Automated Hand Hygiene Monitoring System, Infection Control Today, Jul. 15, 2011, pp. 1-6.

Virtual Patient Observation: Centralize Monitoring of High-Risk Patients with Video-, Cisco Video Surveillance Manager, 2013, pp. 1-6.

Conaire et al., "Fusion Of Infrared and Visible Spectrum Video for Indoor Surveillance", WIAMIS, Apr. 2005, 4 pages.

Hong, Eliane, "[Wohit] Hand Hygiene Being Taught in Hospitals via Social Gaming", L'Atelier BNP Paribas, Health, Apr. 2014, 6 pages.

Mooney, Tom, "Rhode Island ER First To Test Google Glass on Medical Conditions", EMS1, retrived from <https://www.ems1.com/ems-products/technology/articles/1860487-Rhode-Island-ER-first-to-test-Google-Glass-on-medical-conditions/>, Mar. 10, 2014, 3 pages.

Quan et al., "Facial Asymmetry Analysis Based on 3-D Dynamic Scans", 2012 IEEE International Conference on Systems, Man, and Cybernetics; COEX, Seoul, Korea; DOI: 10.1109/ICSMC.2012.6378151, Oct. 14-17, 2012, pp. 2676-2681.

Raheja et al., "Human Facial Expression Detection From Detected in Captured Image Using Back Propagation Neural Network", International Journal of Computer Science and Information Technology (IJCSIT), vol. 2, No. 1, Feb. 2010, pp. 116-123.

Non-Final Office Action received for U.S. Appl. No. 17/152,403, dated Mar. 15, 2022, 10 pages.

Non-Final Office Action received for U.S. Appl. No. 17/101,639, dated Aug. 2, 2022, 13 pages.

Notice of Allowance received for U.S. Appl. No. 17/318,521, dated Aug. 31, 2022, 9 pages.

Otanasap et al., "Pre-Impact Fall Detection System Using Dynamic Threshold and 3D Bounding Box", SPIE.Digital Library, Proceedings vol. 10225, Eighth International Conference on Graphic and Image Processing (ICGIP 2016), Available online at: <https://doi.org/10.1117/12.2266822>, Feb. 8, 2017, pp. 1-6.

Zarka et al., "Real-Time Human Motion Detection and Tracking", IEEE, Available online at: <https://ieeexplore.ieee.org/document/4530098>, 2008, pp. 1-6.

* cited by examiner

METHODS AND SYSTEMS FOR DETECTING STROKE SYMPTOMS

CROSS-REFERENCE TO RELATED APPLICATION

This application claims the benefit of U.S. patent application Ser. No. 16/816,626, filed Mar. 12, 2020 and titled "Methods and Systems for Detecting Stroke Symptoms," which claims the benefit of U.S. Pat. No. 10,614,288, filed Dec. 30, 2016 and titled "Methods and Systems for Detecting Stroke Symptoms," which claims the benefit of U.S. Provisional Patent Application No. 62/273,735, filed Dec. 31, 2015 and titled "Methods and Systems for Detecting Stroke Symptoms," each of which is herein incorporated by reference in their entireties.

TECHNICAL FIELD

The present disclosure relates to computerized methods and systems for detecting stroke symptoms.

BACKGROUND

A stroke occurs when a portion of the brain has insufficient blood flow. There are generally two kinds of strokes, hemorrhagic and ischemic. Hemorrhagic stroke occurs when a blood vessel in the brain ruptures or leaks. This can prevent other areas of the brain from receiving adequate blood flow, as well as creating pressure and other injuries in the area of the rupture or leak. Ischemic stroke occurs when a blood vessel in the brain becomes at least partially blocked, preventing a full supply of blood from passing the blockage to reach other areas of the brain. Stroke may also refer to a transient ischemic attack (TIA), where blood flow to part of the brain is temporarily interrupted, but is restored without intervention. A TIA may be, but is not always, a precursor to a stroke. A person who has experienced a TIA is generally considered at higher risk for stroke than someone who has not experienced a TIA.

Although different people may experience stroke differently, symptoms for hemorrhagic and ischemic stroke, as well as TIA, are generally similar. Symptoms may include slurred, garbled, or nonsense speech and physical asymmetry. For example, a person experiencing a stroke or TIA may have difficulty holding an arm up in an extended position for even a short period of time—the stroke victim may need assistance to lift the arm or may be unable to hold the arm in a raised position, even if the other arm can easily be raised and held in a raised position. As another example, a person experiencing a stroke or TIA may have a visually perceptible droop or sagging in the face, shoulders, or other body carriage. The droop or sagging may be pronounced, or the asymmetry may be most noticeable with movement, such as when the person smiles or speaks. Typically, weakness and/or drooping are one-sided, occurring predominantly or entirely on the right or left side of the body, depending on what part of the brain is affected by the stroke.

Stroke can be treated, however, currently available treatments require prompt action. Medication for ischemic stroke is best delivered within 4-6 hours of the onset of symptoms. Hemorrhagic stroke may require even faster intervention, depending on the severity and location of the rupture or leak. A TIA by definition does not require intervention, however, recognizing the occurrence of a TIA is important to allow for diagnostic and preventative care.

BRIEF SUMMARY

This brief summary is provided as a general overview of the more detailed disclosure which follows. It is not intended to identify key or essential elements of the disclosure, or to define the claim terms in isolation from the remainder of the disclosure, including the drawings.

This disclosure generally relates to systems and methods for detecting stroke symptoms. Generally, and without limitation, the method involves collecting a series of images of a person's face. The system identifies reference points on the person's face, for example, points along the cheeks, jowls, and/or brow. The system may superimpose an x-y plane over the reference points in a digital image. The system then monitors images of the face of the person over time. Using the x-y plane (and, optionally, a z-axis), the system compares the positions of the reference points over time. If an asymmetric change in the positions of the reference points is detected, the system generates an alert that the person may be experiencing a stroke.

In some aspects, this disclosure relates to a method for detecting stroke symptoms. The method may comprise receiving from a 3D motion sensor a series of two or more images of the face of a person. The method may comprise superimposing an x-y plane over a plurality of reference points related to anatomical features of the person. The method may comprise comparing, over time, positions of the plurality of reference points relative to the x-y plane. The method may comprise assessing a maintenance of symmetry of the plurality of reference points.

The method may comprise assessing symmetry about an x-axis, a y-axis, and a z-axis. The method may comprise identifying a minimum asymmetric change in the positions of the plurality of reference points. The method may comprise evaluating whether the minimum asymmetric change is maintained for a minimum period of time. The method may comprise alerting a designated recipient of an asymmetric change. The method may further comprise superimposing a z-axis over the plurality of reference points. The method may further comprise using the z-axis at least in part to assess the maintenance of symmetry of the plurality of reference points over time. The method may comprise communicating the series of images of the face of the person to a central monitoring station. The method may comprise displaying a series of images for a plurality of people being monitored on a primary display at the central monitoring station. The method may comprise alerting the central monitoring station if an asymmetric change in the positions of the plurality of reference points relative to the x-y plane is identified. The method may comprise displaying images of the person for whom the asymmetric change was identified on a central monitoring station alert display upon receiving an alert.

In some aspects, this disclosure relates to a system for detecting stroke symptoms. The system may comprise one or more 3D motion sensors. The one or more 3D motion sensors may be located to provide the one or more 3D motion sensors with a view of the face of a person to be monitored. The 3D motion sensors may be configured to collect a series of images of the face of the person. The system may comprise a computerized monitoring system. The computerized monitoring system may be communicatively coupled to the one or more 3D motion sensors. The computerized monitoring system may be configured to identify a plurality of reference points on the face of the person to be monitored. The computerized monitoring system may be configured to superimpose an x-y-z axis system over the plurality of reference points on the face of the person. The computerized monitoring system may be configured to monitor positions of the plurality of the reference points of the face of the person on the x-y-z axis system. The stroke detection system may comprise a computerized communication system. The computerized communication system may be communicatively coupled to the computerized monitoring system. The computerized communication system may be configured to send an alert to one or more designated recipients if a minimum asymmetric change in the position of the reference points relative to the x-y-z axis system is identified. The computerized communication system may be configured to send an alert if the minimum asymmetric change is maintained for a minimum period of time.

The stroke detection system may further comprise a central monitoring station. The central monitoring station may be communicatively coupled to the computerized communication system. The central monitoring station may be configured to display at least a portion of the series of images of the person. The central monitoring station may comprise a primary display. The central monitoring station may comprise an alert display. The alert display may be a dedicated portion of the primary display. The alert display may be a separate display or series of displays from the primary display. If the computerized monitoring system detects an asymmetric change in the positions of the plurality of the reference points on the face of the person on the x-y-z axis system, the computerized communication system may be configured to send an alert to the central monitoring station. The central monitoring station may be configured to move the display of at least a portion of the series of images of the person from the primary display to the alert display upon receipt of an alert.

In some aspects, this disclosure relates to computer-readable storage media having embodied thereon computer-executable instructions. When executed by one or more computer processors, the instructions may cause the processors to receive from a 3D motion sensor a series of two or more images of the face of a person. The instructions may cause the processor(s) to superimpose an x-y plane over a plurality of reference points related to anatomical features of the person. The instructions may cause the processor(s) to compare, over time, the position of the plurality of reference points relative to the x-y plane. The instructions may cause the processor(s) to assess the maintenance of symmetry of the plurality of reference points over time. The instructions may cause the processor(s) to identifying asymmetric change in the positions of the plurality of reference points. The instructions may cause the processors to alert a designated recipient of the asymmetric change. The instructions may cause the processor(s) to display a series of images for a plurality of people being monitored on a primary display at a central monitoring station. The instructions may cause the processor(s) to alert the central monitoring station if an asymmetric change in the positions of the plurality of reference points is identified. The instructions may cause the processor(s) upon receiving an alert to cause the central monitoring station to duplicate the display of the series of images associated with the alert on a central monitoring station alert display.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The description references the attached drawing figures, wherein.

DETAILED DESCRIPTION

Some individuals may be at higher risk of stroke than others. There seem to be hereditary components to stroke, so those with a family history of stroke may have a higher risk than others with no family history of stroke. Certain medications or medical procedures may increase the risk of stroke, sometimes for a relatively short period. For example, some surgical interventions can cause blood clots that can break away from the surgical site and be swept through the blood vessels to the brain, where smaller blood vessels may trap the clot, causing an ischemic stroke. That risk may be present for days or weeks after the surgery, and then decrease significantly as the surgical site heals and blood clots are less likely to form. People who have had a stroke before may be more likely to have a stroke again. For these and other reasons, some people may be at higher risk of stroke than others, and may merit monitoring for stroke symptoms.

A common stroke symptom is an atypical asymmetry in facial features, often described as a one-sided droop. Most people have some asymmetry between the left and right sides of their faces (e.g., about an imaginary y-axis run down the center of the person's face), but a person having a stroke may lose involuntary as well as voluntary muscle control, sometimes resulting in a distinct sagging of one or more features on one side of the face. The sagging may be observed in the mouth, for example, where one corner of the mouth might be appreciably lower than the other. The sagging may be most noticeable when the person tries to smile or speak, with one side of the mouth responding, and the other side of the mouth unresponsive and/or sagging. Sagging may also be observed in the eyebrows, eyelids, cheeks, or jowls.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
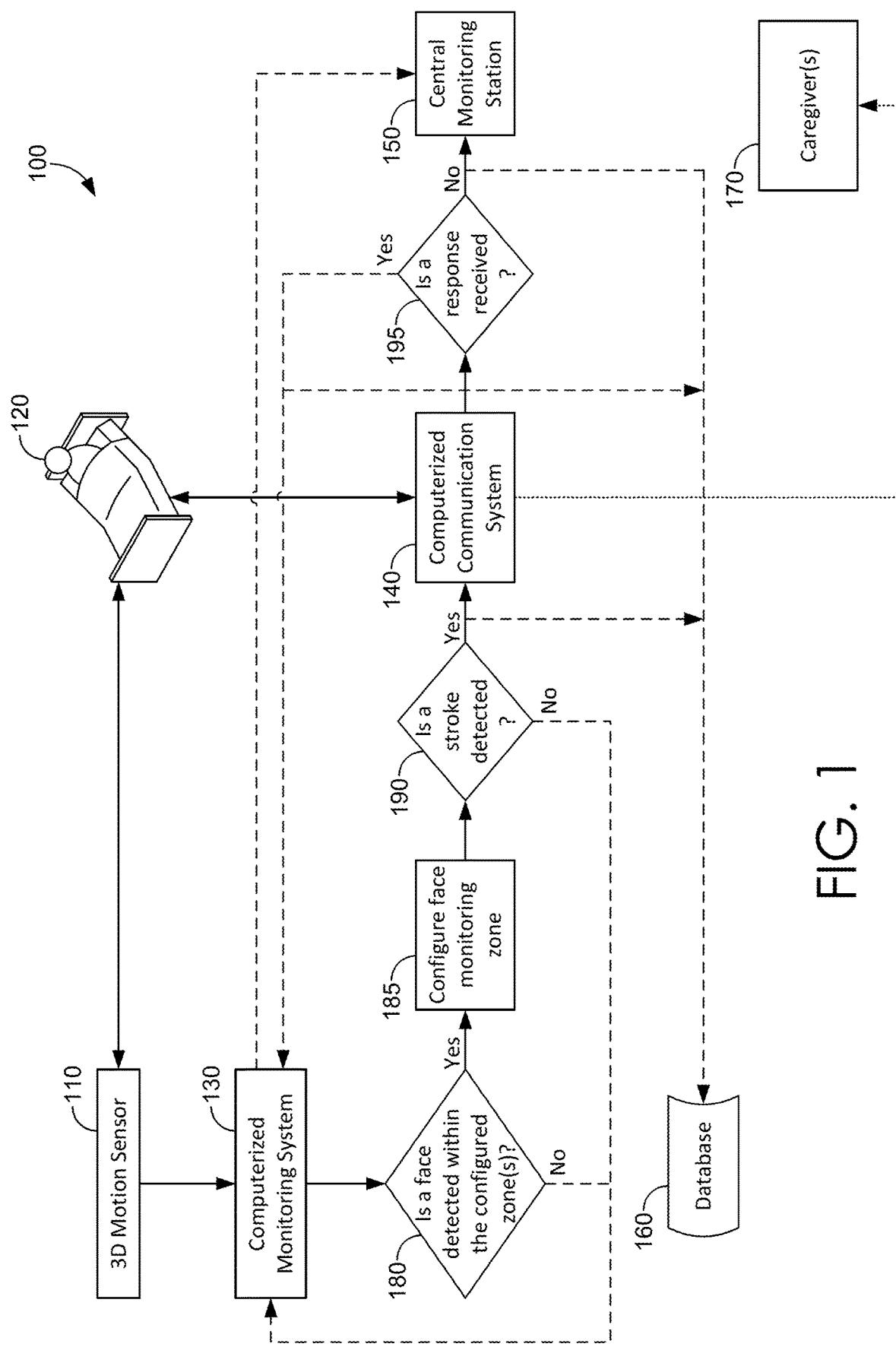
FIG. 1 is an exemplary flowchart for a stroke detection system.

As shown in FIG. 1, a system for detecting stroke symptoms 100 may include one or more 3D motion sensors 110. A 3D motion sensor is an electronic device that contains one or more cameras capable of identifying individual objects, people, and motion. The 3D motion sensor may further contain one or more microphones to detect audio. The cameras can utilize technologies including but not limited to color RGB, CMOS sensors, lasers, infrared projectors, and RF-modulated light. The 3D motion sensor may have one or more integrated microprocessors and/or image sensors to detect and process information both transmitted from and received by the various cameras. Exemplary 3D motion sensors include the Microsoft® Kinect® Camera, the Sony® PlayStation® Camera, and the Intel® RealSense™ Camera, each of which happens to include microphones, although sound capture is not essential to the practice of the disclosure.

As used herein, "a sensor" and "sensors" are used interchangeably in the singular and plural unless expressly described as a singular sensor or an array of sensors. A singular sensor may be used, or a sensor may comprise two or more cameras integrated into a single physical unit. Alternately, two or more physically distinct sensors may be used, or two or more physically distinct arrays of sensors may be used.

A 3D motion sensor 110 may be co-located with a person 120 to be monitored. The person 120 to be monitored may be monitored in a variety of environments, including, without limitation, a hospital, a home, a hospice care facility, a nursing home, an assisted living facility, an outpatient medical care facility, and the like. The 3D motion sensor 110 may be positioned where it is likely to capture images of the face of the person 120 to be monitored. For example, a 3D motion sensor 110 may be oriented to take images of a bed, chair, or other location where the person 120 to be monitored may spend a significant amount of time. The 3D motion sensor 110 may be permanently installed, or may be temporarily set up in a room as needed. The person 120 to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 110 may communicate data, such as images of the person 120 being monitored, to a computerized monitoring system 130. The computerized monitoring system 130 is a computer programmed to monitor transmissions of data from the 3D motion sensor 110. The computerized monitoring system 130 may be integral to the 3D motion sensor 110 or a distinctly separate apparatus from the 3D motion sensor 110, possibly in a remote location from 3D motion sensor 110 provided that the computerized monitoring system 130 can receive data from the 3D motion sensor 110. The computerized monitoring system 130 may be located in the monitored person's room, such as a hospital room, bedroom, or living room. The computerized monitoring system 130 may be connected to a central monitoring station 150. The computerized monitoring system 130 and central monitoring station 150 may be remotely located at any physical locations so long as a data connection exists (USB, TCP/IP or comparable) between the computerized monitoring system 130, the computerized communication system 140 (if separate from computerized monitoring system 130), the central monitoring station 150, and the 3D motion sensor(s) 110.

Figure 3A:
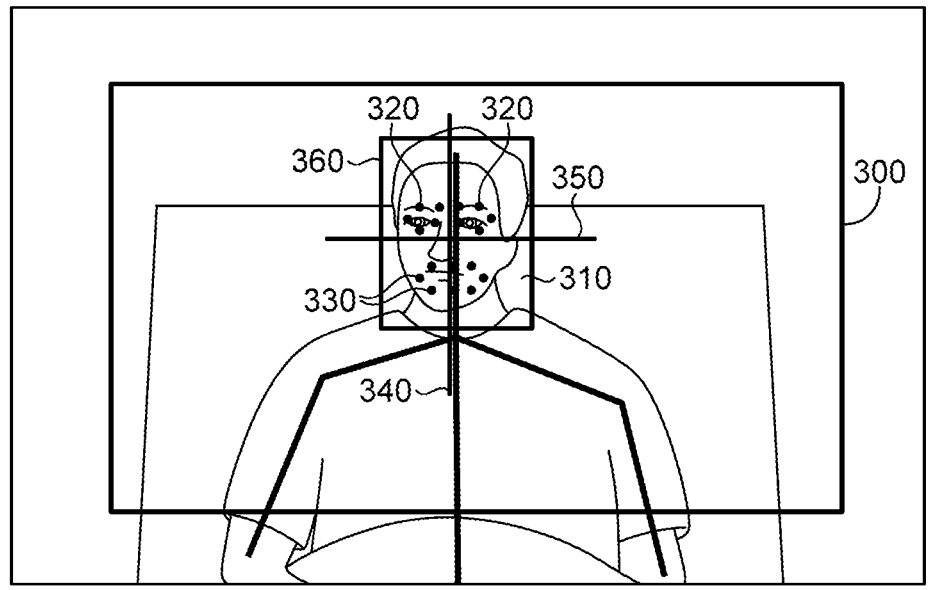
FIGS. 3A and 3B are exemplary configurations for a face monitoring zone.

The computerized monitoring system 130 may receive data from 3D motion sensor 110. The data may include images of a monitoring zone 300, as shown in FIG. 3A. At step 180, the computerized monitoring system 130 may assess whether a face is detected within monitoring zone 300. If a face is not detected within the monitoring zone 300 at step 180, the computerized monitoring system 130 may continue to analyze images for facial features in monitoring zone 300 as long as 3D motion sensor 110 continues to transmit data.

If a face is detected within the monitoring zone 300 at step 180, computerized monitoring system 130 may, at step 185, configure a face monitoring zone 310. Configuring the face monitoring zone 310 may include digitally superimposing an x-y plane over the face detected in the image data. The face monitoring zone 310 may include a frame 360 around the face detected in the image data. Frame 360 is shown in FIG. 3A as rectangular, however, other shapes could be used, including, without limitation, squares, circles, ovals, triangles, and irregular shapes. Frame 360 may help the computerized monitoring system 130 "lock on" to a particular person's face. Locking on to a particular face may be helpful if, for example, a visitor or caregiver may get very near the person 120 being monitored, such that the system might otherwise inadvertently switch from tracking the person 120 being monitored, following instead the face of the visitor or caregiver that entered the monitoring zone 300.

In addition to or in lieu of superimposing a frame 360 around the face detected in the image data, computerized monitoring system 130 may digitally superimpose over the face an x-y plane, such as y-axis 340 and x-axis 350. The y-axis may be placed generally along the bridge of the nose, roughly dividing the face into two halves, with one eye on each side of the y-axis 340. The x-axis 350 may be placed roughly halfway between the top of the head and/or hairline and the bottom of the chin. Reference points may be assigned to distinctive features of the face. For example, in FIG. 3A, there are reference points 320 around the eyes, and reference points 330 around the mouth of the person 120 being monitored. It should be understood that the selection of the reference points may vary with the individual and/or the configuration of the monitoring system 100. For example, if infrared cameras are used, time of flight analysis may be used to determine the distance of an object or reference point from the 3D motion sensor 110, and/or may be used to provide symmetry analysis using a z-axis 810, as described below. As another example, if bandages or physiological anomalies would complicate the tracking of routine reference points, alternative reference points may be assigned. The monitoring zone 300, face monitoring zone 310, reference points 320, 330, frame 360, x-axis 350, and/or y-axis 340 may be configured automatically by the monitoring system 100, may be configured automatically by the monitoring system 100 subject to confirmation and/or modification by a system user, or may be configured manually by a system user.

Figure 3B:
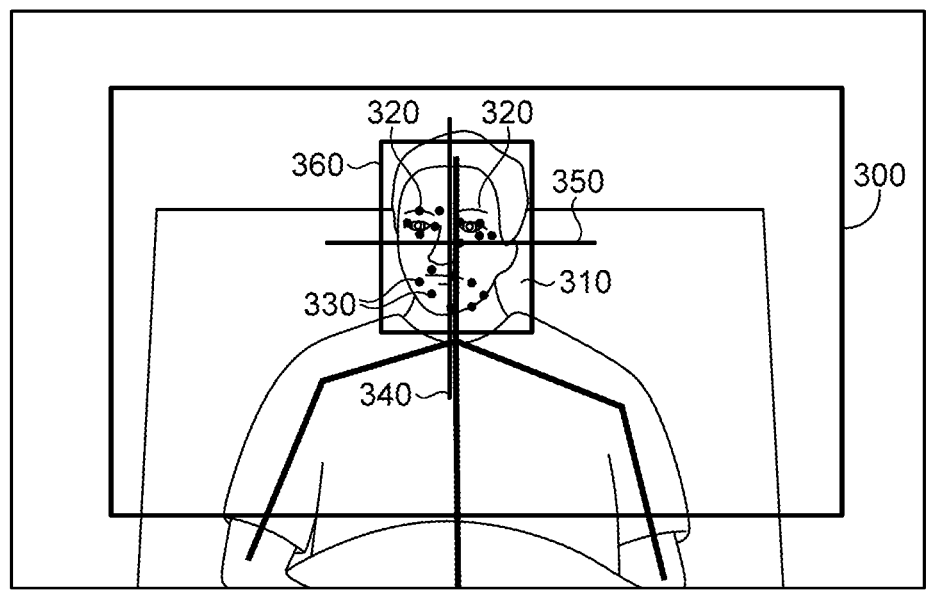

Returning to FIG. 1, at step 190, the computerized monitoring system determines whether a stroke is detected. Step 190 looks for stroke symptoms, in particular, asymmetric changes in the facial features of the person 120 being monitored. By comparing facial images over time, computerized monitoring system 130 can use the facial monitoring zone 310 and reference points 320, 330 to determine whether asymmetric changes in the person's face have occurred. FIG. 3B, for example, may be compared to an earlier acquired image in FIG. 3A of person 120. As shown in FIG. 3B, the reference points 320 and 330 are no longer symmetric about y-axis 340. The asymmetry represents a change from the image in FIG. 3A, where reference points 320, 330 are more symmetrical about y-axis 340 than they are in FIG. 3B. Most individuals have some physical asymmetry, and so testing for a change in symmetry may be more helpful than testing for absolute symmetry. Alternately or additionally, the computerized monitoring system 130 could evaluate deviation from absolute symmetry about y-axis 340 and/or a change in position of reference points 320, 330 relative to x-axis 350. A timer may be employed to evaluate whether the asymmetry or change in position of the reference points persists for a minimum amount of time, which could help distinguish asymmetric facial gestures, like an eyebrow raised in skepticism, from stroke symptoms.

In some embodiments, a certain degree of change in the symmetry or relative symmetry about the x-, y-, and/or z-axes, such as a change in distance of at least 10%, or at least 3 mm, may be required before issuing an alert. These examples are intended to be non-limiting, and any desired percentage or distance may be used. For example, an alarm limit may be set to require a change in distance of at least 5%, or at least 10%, or at least 15%, or at least 20% or more. As another example, an alarm limit may be set to require a change of at least 1-5 mm. Additionally or alternatively, other measures of variance could be used, such as standard deviations, and measures may be based on absolute or relative values. Summed variances, such as the sum of the variances relative to the x-, y- and/or z-axes, or any subcombination thereof, could be used as a minimum variance threshold for issuing an alert.

On detecting facial features and/or a change in facial features consistent with a stroke symptom, computerized monitoring system 130 may communicate the detected stroke symptom to computerized communication system 140. Computerized communication system 140 may be configured to send an alert of the stroke symptom to one or more designated recipients. Computerized communication system 140 may be an integral part of computerized monitoring system 130 and/or may be implemented using separate software, firmware, and/or hardware, possibly physically remote from computerized communication system 140.

When an alert is triggered, the alert may be sent, at least initially, to the person 120 being monitored, to give the person 120 being monitored an opportunity to respond before alerting the central monitoring station 150 and/or caregiver(s) 170. For example, an audible message may be played in the room where person 120 is being monitored, possibly asking something like, "Are you ok?" or "Do you need help?" Shown as step 195 in FIG. 1, computerized monitoring system 130 can analyze subsequent image data from 3D motion sensor 110 for gestures, such as a head nod, consistent with a yes or no answer. If 3D motion sensor 110 is equipped with microphones, computerized monitoring system 130 can analyze sound data for recognizable words, such as yes, no, help, or even certain extended sounds, such as "oooooohhhhhhhhh," which might be consistent with moaning or other vocalization associated with pain, discomfort, or disorientation.

Central monitoring station 150 may be alerted if no response is received at step 195, or if the response is unintelligible or indicates that the person 120 being monitored wants or needs assistance. Alternately, or additionally, central monitoring station 150 may be alerted with or even before person 120, so that central monitoring station 150 can determine whether the apparent stroke symptom detected is, in fact, problematic. On receiving an alert, the central monitoring station 150, or an attendant there, may view live image, video, and/or audio feed from the 3D motion sensor 110, and evaluate whether the automated observations are persistent and/or troubling. If person 120 has been alerted by the computerized communication system 140, central monitoring station 150 or an attendant there can use the data from 3D motion sensor 110 to evaluate whether a response from person 120 is reassuring or indicates that person 120 requires assistance. Central monitoring station 150 and/or computerized monitoring system 130 may analyze the response from person 120, however, if the response does not include words or gestures recognizable by the computerized system, an attendant at central monitoring station 150 may be able to interpret the person's response. If needed, the central monitoring station 150 and/or the attendant could then approve alert(s) to appropriate caregiver(s) 170 and/or call for emergency assistance (e.g., send a request for emergency medical services to 9-1-1 or a similar service local to the person 120).

One or more caregiver(s) 170 local to person 120 can be alerted with or even before person 120 and/or central monitoring station 150, so that the caregiver(s) 170 can assess what is happening in person. Or, monitored person 120, caregiver(s) 170, and the central monitoring station 150 could all be alerted at the same time. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if stroke symptoms are detected, and no response from person 120 or a caregiver 170 is received or observed) or repeated alerts (two or more distinct events where possible stroke symptoms are observed). The priority and timing of alerts to different individuals may be different for initial, continuing, and/or repeated alerts.

Data associated with alerts may be logged by computerized monitoring system 130 and/or central monitoring station 150 in a database 160. Data associated with an alert may include, without limitation, the telemetry data from 3D motion sensor 110 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof.

Figure 2:
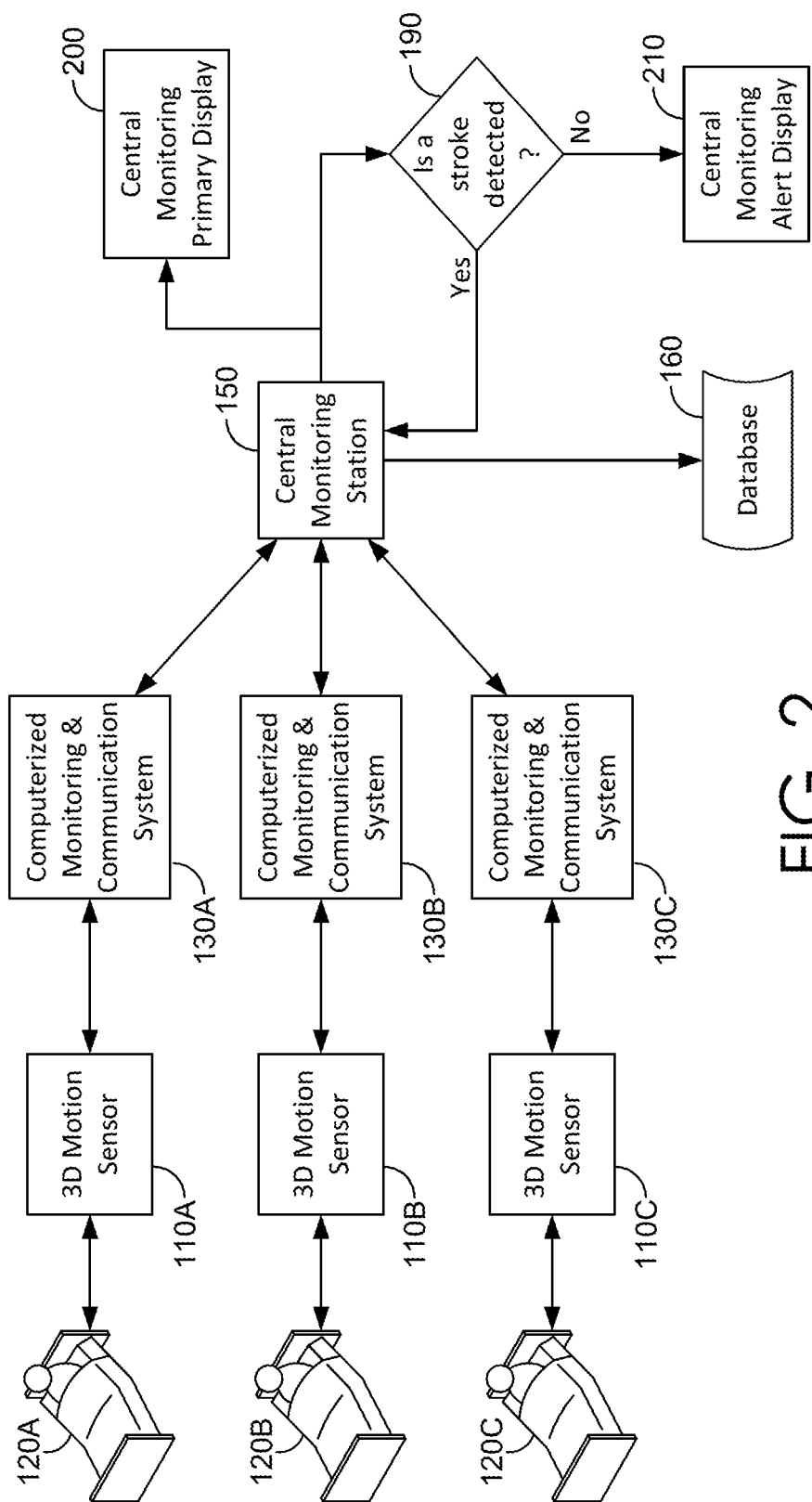
FIG. 2 is an exemplary flowchart for a central monitoring station for a stroke detection system.
Figure 4:
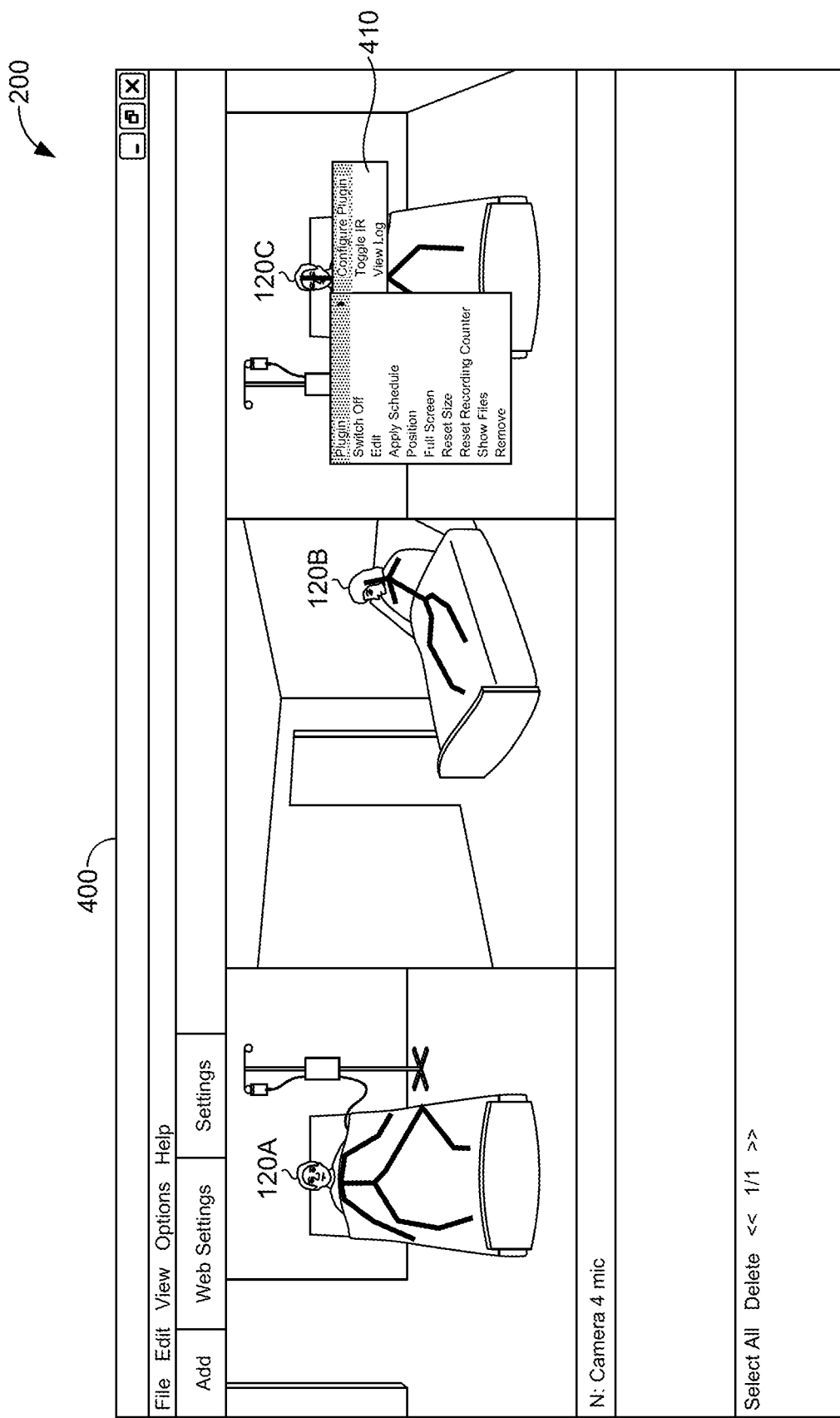
FIG. 4 is an exemplary display for a stroke detection system.

As shown in FIG. 2, central monitoring station 150 may receive data from multiple computerized monitoring systems, 130A, 130B, and 130C. For simplicity, the computerized communication system associated with each computerized monitoring system is shown as an integrated component of the computerized monitoring system. If desired, separate computerized communication systems and/or a shared computerized communication system could be used. Computerized monitoring systems 130A, 130B, and 130C receive data from 3D motion sensors 110A, 110B, and 110C, which are, respectively, monitoring persons 120A, 120B, and 120C. Data received by the central monitoring station 150 from computerized monitoring systems 130A, 130B, and 130C may routinely be displayed on central monitoring primary display 200. A single primary display 200 may display data from more than one computerized monitoring system, shown as view 400 in FIG. 4. Alternately, primary display 200 may comprise two or more distinct screens, each of which may display data from one or more computerized monitoring systems. As shown, the display for monitored person 120C has an open configuration window 410, which is described in greater detail below.

When the central monitoring station 150 receives an alert from any of the computerized monitoring and communication systems 130A, 130B, 130C, indicating that a monitored person 120A, 120B, or 120C is presenting one or more stroke symptoms, audio and/or alert information for that particular person may be displayed on the central monitoring alert display 210. An alert can be presented in a variety of formats. An alert may be a visual cue on screen at the central monitoring station 150, such as the specific camera view flashing or being highlighted in a color to draw attention to that display among others. An alert may be an audible sound (e.g., a voice or alarm type sound) at the central monitoring station 150, an audible sound at the computerized monitoring system 130 attached to the 3D motion sensor 110, a text message, an email, turning on a light or even running a program on a computer. Should the central monitoring station 150 receive alerts from more than one of the computerized monitoring and communication systems 130A, 130B, 130C, indicating that a person 120A, 120B, and/or 120C is presenting a stroke symptom, the central monitoring alert display 210 may display the video, audio, and/or alerting information from all such instances at the same time. If no alert is received by the central monitoring station 150, it may be that nothing is displayed on the central monitoring alert display 210. Preferably, all monitored individual rooms can be displayed and visible on the central monitoring primary display 200 whether alerting or not. When an alert is generated, attention can be drawn to the particular camera on central monitoring primary display 200 and/or a duplicative display of the alerting camera can be displayed on a second separate computer monitor, e.g., the central monitoring alert display 210.

An electronic record of any alerts received, any responses to the alert observed or received, and/or any actions taken by the central monitoring station 150 can be stored in a database 160.

Figure 5:
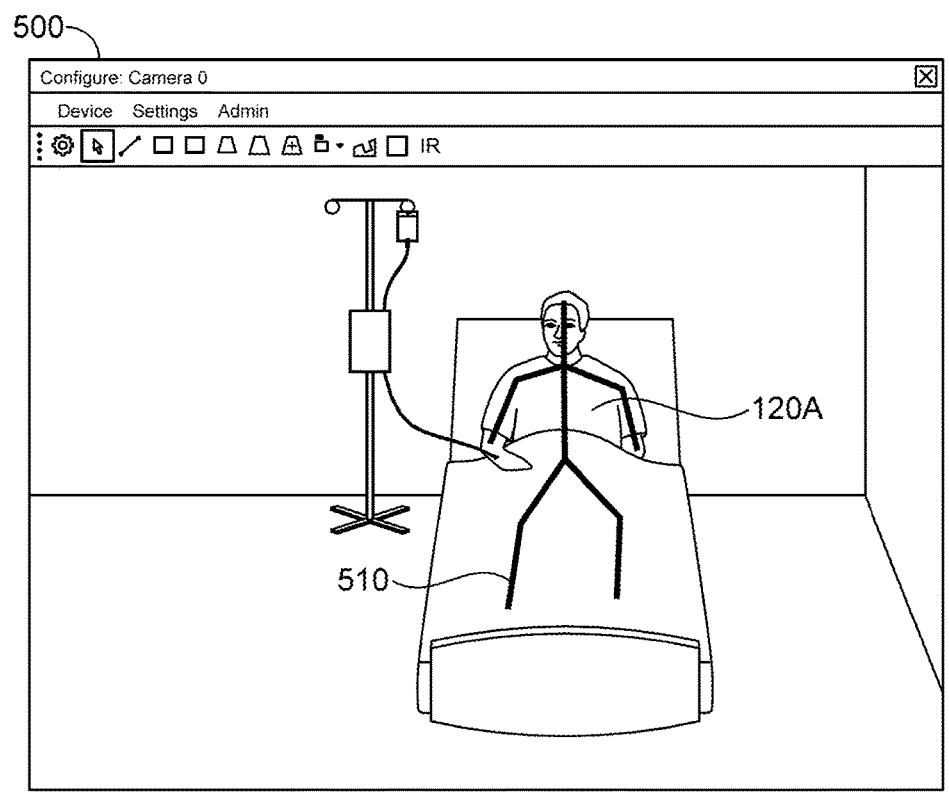
FIG. 5 is an exemplary configuration view for a stroke detection system.
Figure 6:
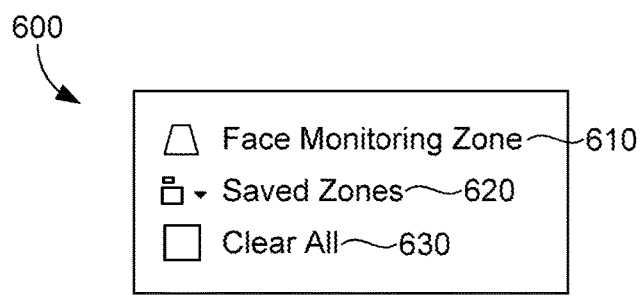
FIG. 6 is an exemplary configuration menu for a stroke detection system.

As mentioned above, FIG. 4 shows an exemplary view 400 for central monitoring primary display 200, including video data for multiple monitored persons 120A, 120B, and 120C displayed on a single screen. FIG. 5 shows an alternative view 500 for central monitoring primary display 200, including image data for only monitored person 120C. The view includes a skeletal FIG. 510, which may be identified by central monitoring station 130A, and used to track or "lock on to" the person 120C. A skeletal FIG. 510 is shown in FIG. 5, however, alternate image analysis could be used, including, without limitation, blob recognition, facial tracking, facial recognition, or the visual or electronic identification of a badge or transmitter. No zones are marked in the image of FIG. 5. FIG. 6 shows an exemplary configuration menu 600, with an option 610 for configuring a face monitoring zone, an option 620 for configuring other saved zones, and an option 630 to clear all configured zones.

Figure 7:
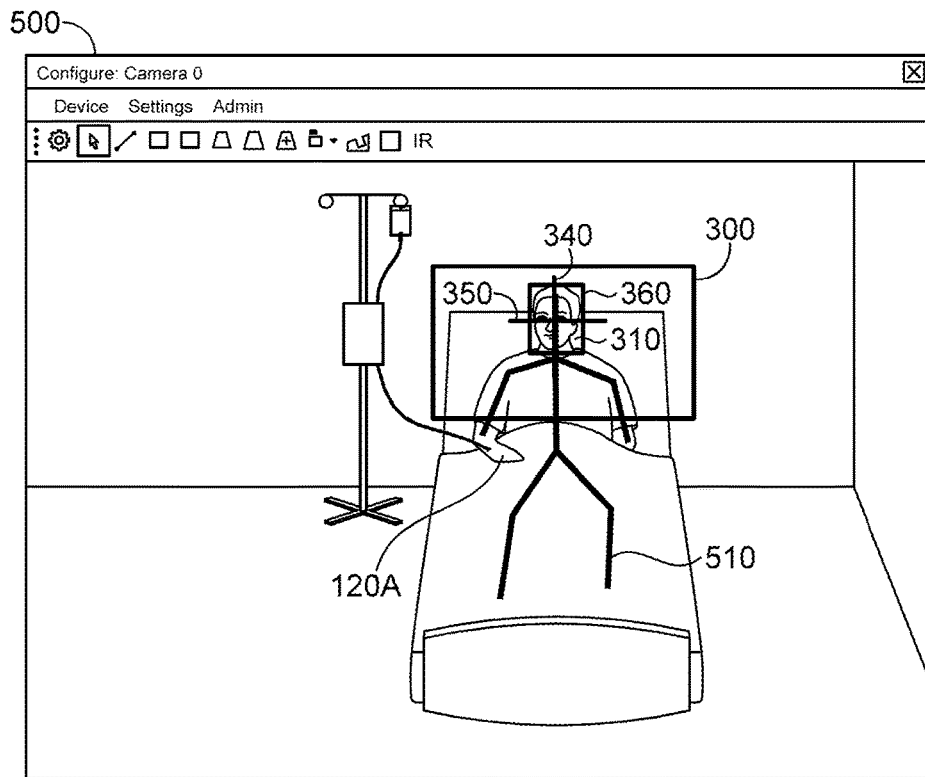
FIG. 7 is an exemplary configuration view for a stroke detection system.

FIG. 7 shows view 500 as it might appear on selecting a menu option to configure one or more zones. FIG. 7 shows a monitoring zone 300 generally about the upper torso, shoulders, and head of person 120A lying in a hospital bed. Monitoring zone 300 may be configured by the computerized monitoring system 130. For example, monitoring zone 300 may be defined as a fixed perimeter or volume around the head of person 120C, as determined based on analysis using skeleton figure, blob recognition, and/or facial tracking. If configured by the computerized monitoring system 130, a user may be allowed to modify the system-configured monitoring zone 300, or a user may be required or allowed to manually configure the monitoring zone 300. The 3D motion sensor 110 may collect image and/or sound data for a broader portion of a room than just the monitoring zone 300. The computerized monitoring system 130 may analyze only data related to the monitoring zone 300, with or without capturing images and/or sound from a broader portion of the room. This may reduce total processing capacity required, as the most processing-intensive algorithms (e.g., facial tracking, identification and tracking of reference points) are run on a limited data set. Capturing broader image data may help provide context for an alert, e.g., at central monitoring station 150. For example, using image data from most or all of the room, central monitoring station 150 or an attendant there may determine that it is unnecessary to send an alert to a caregiver 170 if there is already a caregiver 170 in the room and tending to the person 120 being monitored at the time of an alert. A monitoring zone 300 may also help stroke detection system 100 "lock on" to a person 120 being monitored, and help avoid situations where a caregiver, visitor, or other person who gets very close to the person 120 being monitored might be tracked after moving away from person 120. If the other person moves out of monitoring zone 300, but person 120 being monitored does not leave monitoring zone 300, stroke detection system 100 will continue to monitor person 120 in monitoring zone 300.

Using facial recognition algorithms, the computerized monitoring system 130 may identify key features of the face of person 120C being monitored. Key features may include, without limitation, the orbit of the eye socket(s), eyebrow(s), eyebrow ridge(s), the nose, the bridge of the nose, the mouth, top of the head, hairline, chin, ears, cheekbones, etc. The features used may vary with the kind of technology (e.g., visible vs. infrared light) and/or prominent or accessible features on person 120C. Using the key features, the computerized monitoring system 130 may center an x-y plane defined by y-axis 340 and x-axis 350 at roughly the center of the person's face. The placement of the y-axis 340, for example, may be conditioned on having one eye and at least a portion of the mouth on each side of y-axis 340. The x-axis 340 may be placed on the location of the upper cheekbone, the orbital bone about the eye socket, the apex of the nose, or the like.

Alternately, the position of frame 360 may be determined, e.g., to circumscribe the head, and the y-axis 340 may divide the frame 360 in half vertically, and the x-axis 350 may divide the frame 360 in half horizontally. The absolute placement of the x-y plane is not essential, as long as the x-y plane can be consistently positioned over new images of person 120, so that the x-y plane provides a constant frame of reference. Since the x-y plane will be used for comparing the position of soft tissue features, if the x-y plane is defined by anatomical features, those features may preferably be bony, cartilaginous, or otherwise unlikely to move, particularly during a stroke or TIA. For example, the ears do not typically sag or droop during a stroke or TIA. As another example, the x-y plane might be situated with the intersection between the y-axis 340 and the x-axis 350 on the tip or apex of the nose of the person 120 being monitored. The computerized monitoring system 130 may use facial tracking rather than facial recognition, facial recognition implying that the software attempts to identify a particular person (e.g., Jane Doe) based on facial features, as opposed to recognizing a particular facial feature (e.g., an eye) using facial tracking. If desired, facial recognition algorithms could also be used, e.g., to confirm that the system has "locked on" to the intended person 120 to be monitored; or to confirm the identity of the monitored person 120 for cross-checking records before recording monitoring data to an electronic medical record, billing system, or the like.

The computerized monitoring system 130 may identify soft-tissue reference points on the face of monitored person 120A. As shown in FIGS. 3A and 3B, exemplary soft-tissue reference points may generally outline the eyes (reference points 320) and/or the mouth (330). Other exemplary soft-tissue reference points, which could be used with or in lieu of the eyes and/or mouth, include the jowls, flesh along the cheekbone, the neck, and the portion of the neck immediately under the chin. The eyes and/or mouth may be preferred as they are easily identified by facial tracking algorithms and tend to be readily visible even if the person 120 to be monitored is wearing a blanket or high-necked clothing.

Figure 8:
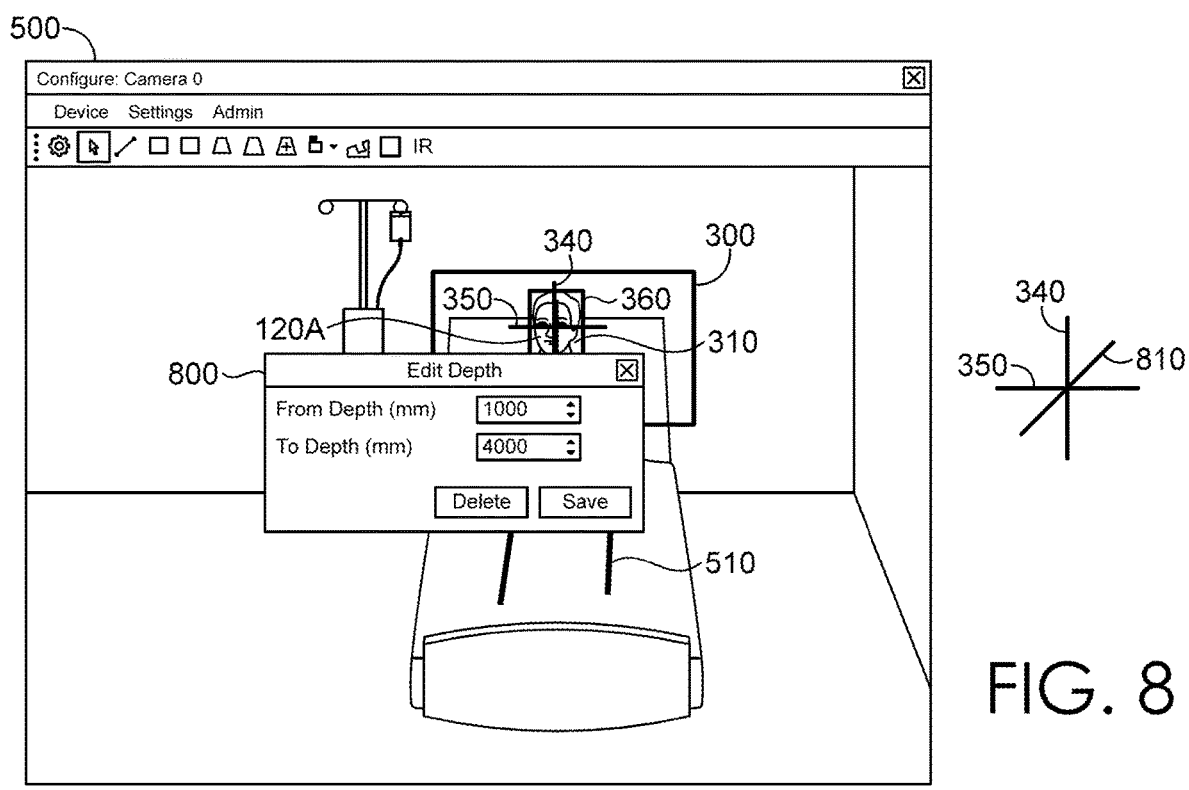
FIG. 8 is an exemplary configuration view for a stroke detection system.

If monitoring zone 300 and/or face monitoring zone 310 are configured by a user, the user may operate an input device to select a point on an image or video from the computerized monitoring station 130. The user may draw a perimeter defining a zone freehand, or may drag the input device (such as an electronic stylus or mouse pointer) from one point to another to define a diagonal axis for the perimeter of the zone. Other configuration options, including drag-and-drop templates and coordinate identification, could be used. A 2D monitoring zone 300 and/or face monitoring zone 310 can be operated as a perimeter, or a third dimension of depth can be specified. As with the perimeter, the computerized monitoring system can define or recommend a depth measurement, or the user can provide the depth measurement. FIG. 8 shows a pop-up menu 800 allowing a user to configure or reconfigure the depth of a monitoring zone. The exemplary pop-up menu 800 solicits a depth parameter specified in millimeters (mm), however, any desired unit of measure could be used, including, without limitation, centimeters (cm), meters (m), inches, feet, and yards. Setting a depth for face monitoring zone 310 enables the use of a z-axis 810, shown in the inset in FIG. 8, in cooperation with the x-y plane defined by y-axis 340 and x-axis 350. The use of a z-axis 810 may provide for more accurate data for analysis, and may, therefore, allow for the detection of less severe asymmetry than if using only an x-y plane. For simplicity, z-axis 810 may not be shown even in configuration views, however, the system can collect and analyze depth data while evaluating symmetry. Changes in the depth or thickness of a reference point relative to z-axis 810 may indicate sagging, even if any corresponding change in position observed relative to the y-axis 340 or x-axis 350 is not above a minimum threshold level to identify the change as a stroke symptom. Any described use of an x-y plane could alternately use an x-y-z volume or axis system, assuming that depth data collection is enabled.

Figure 9:
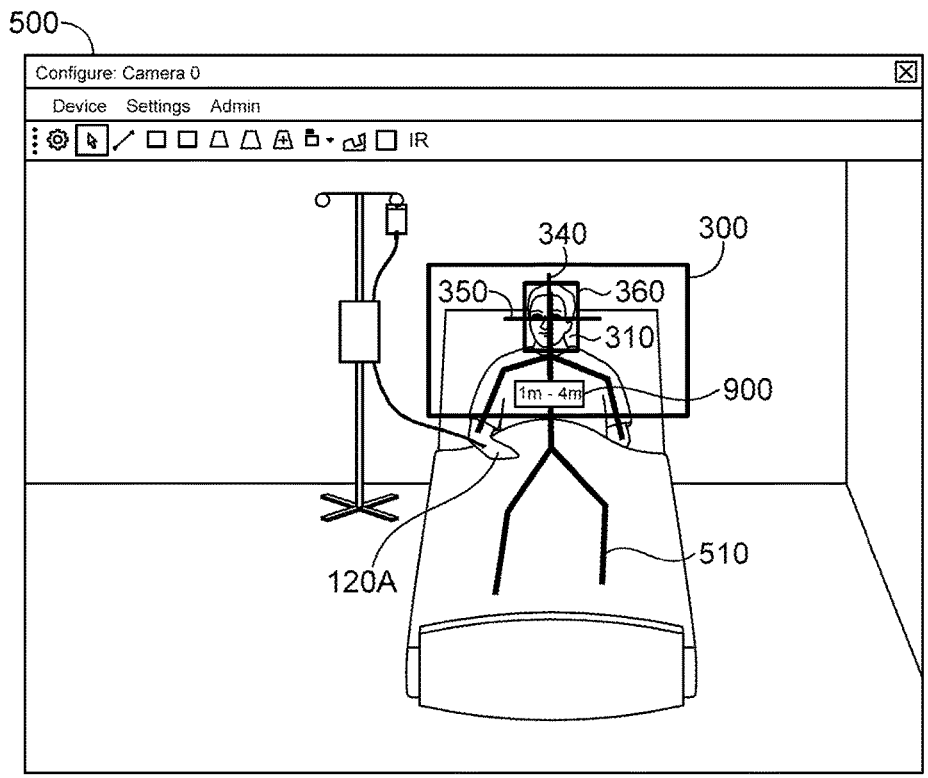
FIG. 9 is an exemplary configuration view for a stroke detection system.

On setting a depth parameter, and while still in a configuration view, the depth of the monitoring zone may be visible as a label 900, as shown in FIG. 9. The depth of monitoring zone 300 and the depth of face monitoring zone 310 may be the same, or they may be configured and/or labeled separately. The depth label 900 may not be visible during routine monitoring and/or alert monitoring, so as not to obscure the person 120 being monitored and/or other activity in any image data from 3D motion sensor 110.

Figure 10:
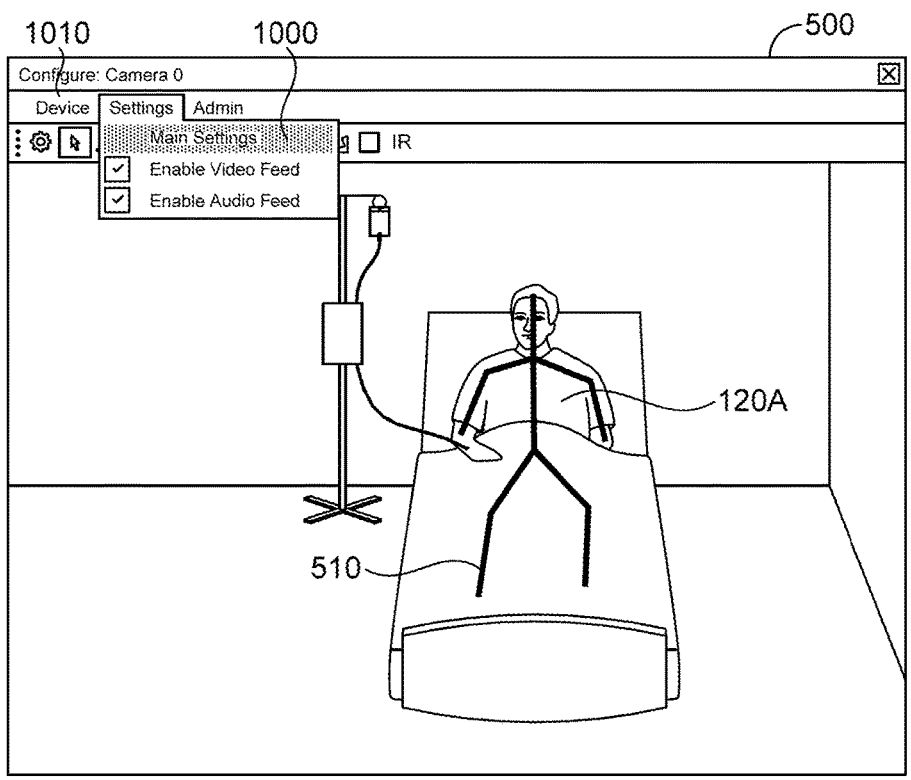
FIG. 10 is an exemplary configuration view for a stroke detection system.

FIG. 10 shows another menu 1000 from configuration view 500. As shown in FIG. 10, a user may be permitted to turn monitoring on or off (e.g., by "unchecking" both video feed and audio feed), or to turn off video feed only, or to turn off audio feed only, if audio feed is available. It may be desirable to disable audio feed, for example, at central monitoring station 150, to prevent overlapping audio feeds from becoming unintelligible noise. If voice or word recognition algorithms are used, those algorithms may run at computerized monitoring system 130 even if audio feed is disabled at a monitoring station, such as central monitoring station 150. On alert or as desired, the audio feed could be enabled for one or more particular person 120 being monitored, e.g., to provide context for an alert. It may be desirable to disable audio and/or video feed to provide some privacy to the person 120 being monitored. For example, it may be desirable to disable audio and/or video feed while the person 120 is being examined by a medical professional, or bathed, or while visitors are present. The need for computerized monitoring for stroke detection is somewhat reduced while the person 120 is interacting with medical professionals, caregivers, or visitors. However, if desired, the audio and/or video feed can be maintained even when there are others with the person 120 being monitored.

Although monitoring zone 300 and face monitoring zone 310 may be configured and operational, they may not be shown outside of the configuration screens for those zones, as in FIG. 10. That is, the zones may be configured and operational, but not superimposed on the images of person 120, so as to permit an unobstructed view of person 120, e.g., at central monitoring station 150 or while configuring other aspects of the stroke detection system.

Figure 11:
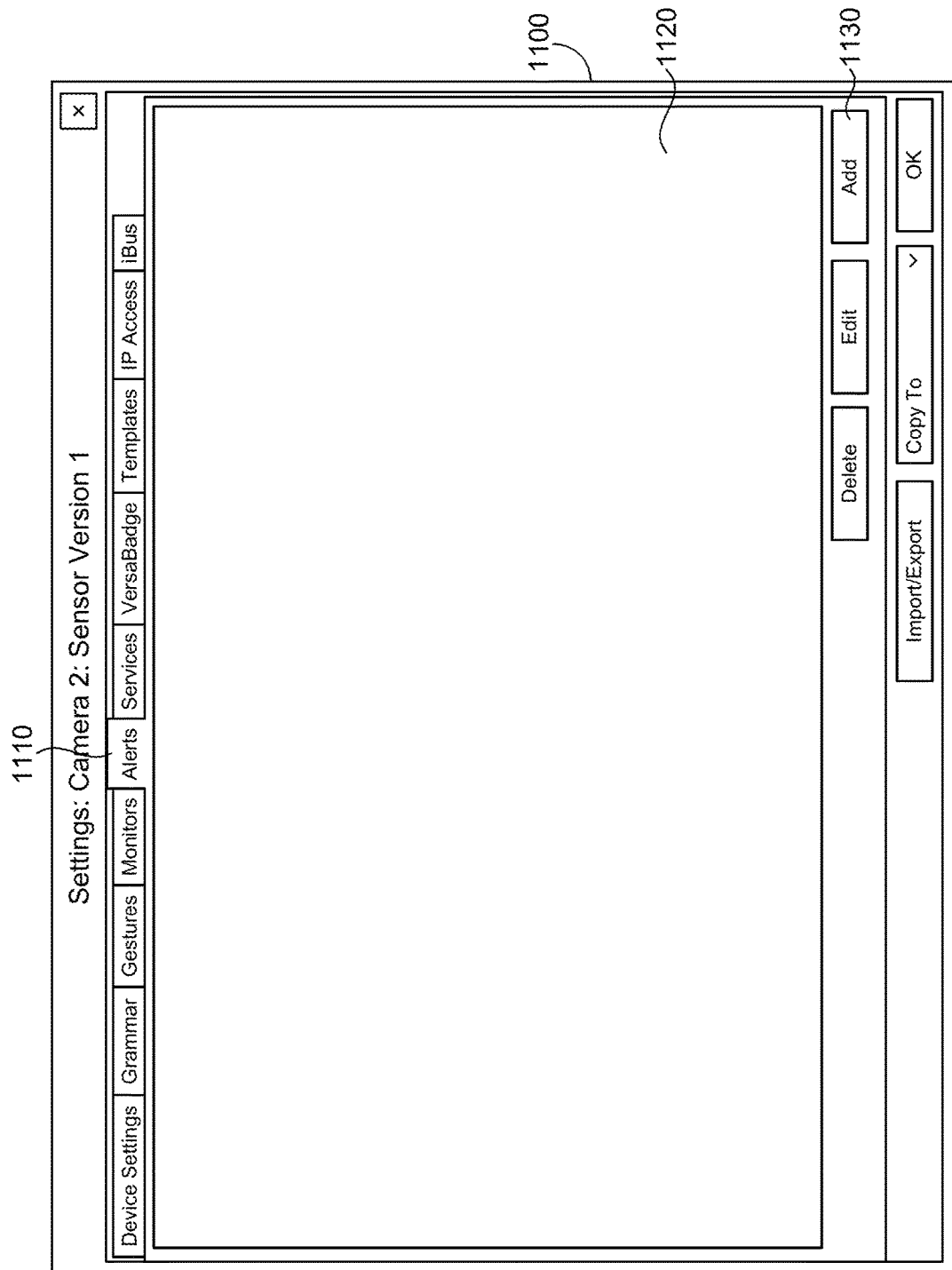
FIG. 11 is an exemplary configuration menu for a stroke detection system.
Figure 12:
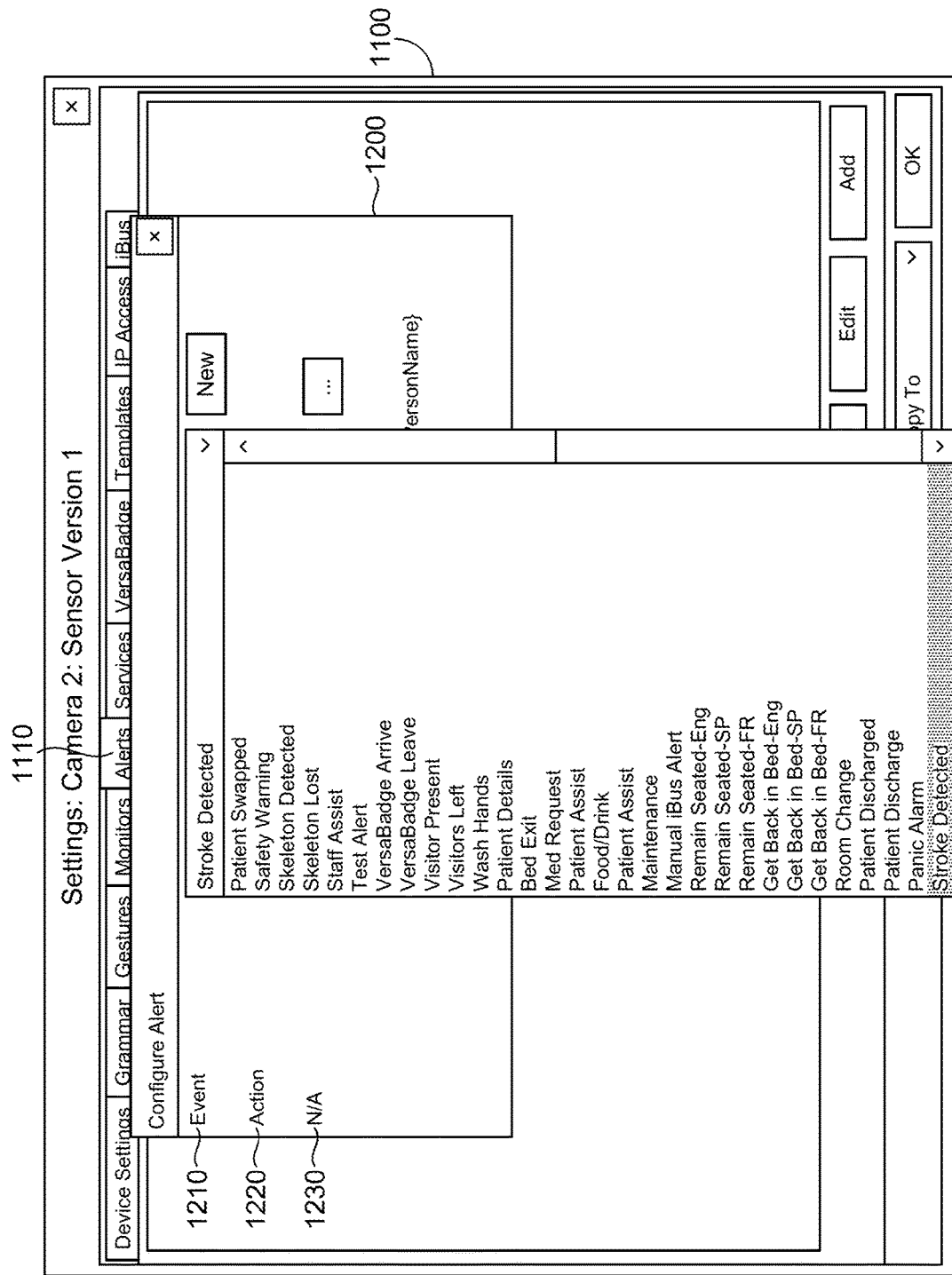
FIG. 12 is an exemplary configuration menu for a stroke detection system.

If the Device menu 1010 in FIG. 10 is selected, the user may see a pop-up menu 1100, as shown in FIG. 11. The use of pop-up, drop down, tabular, or other kinds of menus may be recommended based on, for example, the number and kinds of options associated with a particular menu. However, different kinds of menus could be presented based on user or facility preferences. Pop-up menu 1100 includes a number of tabs, from which a tab for Alerts 1110 has been selected in FIG. 11. The space within the Alerts window 1120 is blank, indicating that no alerts have been configured. If a user selects Add button 1130 at the bottom of the Alerts tab 1110, a new pop-up menu 1200 may appear, as shown in FIG. 12. As shown in FIG. 12, pop-up menu 1200 further includes drop-down menus to configure an alert by specifying an event 1210, an action 1220, and, if applicable, an N/A field 1230. As with the kinds of menus, the particular words used to describe an event, action, and/or NA field may be modified to reflect the environment in which the system is being used, or the facility or personnel using the system or a particular station. For example, a system, station, or user interface may be configured for use in a hospital using clinical terminology. As another example, a remote central monitoring station 150 may have an attendant who is not a medical professional, and lay terminology might be used in lieu of or in addition to clinical terminology. Family or other non-professional and/or non-medical caregivers may have access to the stroke detection system 100 and/or serve as an attendant for a remote monitoring station, and the menus for those users may similarly use descriptive, non-clinical terminology in addition to or in lieu of clinical terminology. Different languages could also be used for different interfaces. As shown in FIG. 12, the stroke detection system 100 may include monitoring and/or alert functions unrelated to stroke detection, as well as the "Stroke Detected" option presented. If desired, other options may be removed from the drop-down menu to simplify user configuration choices for users who do not want or need access to the other functions. Changes to the menus, including changes to the range of menu options and the terminology used in the menus, may be configured when the system is installed or when access is provided to a specific user, and may not require or may not be available for further modification by routine system users.

Figure 13:
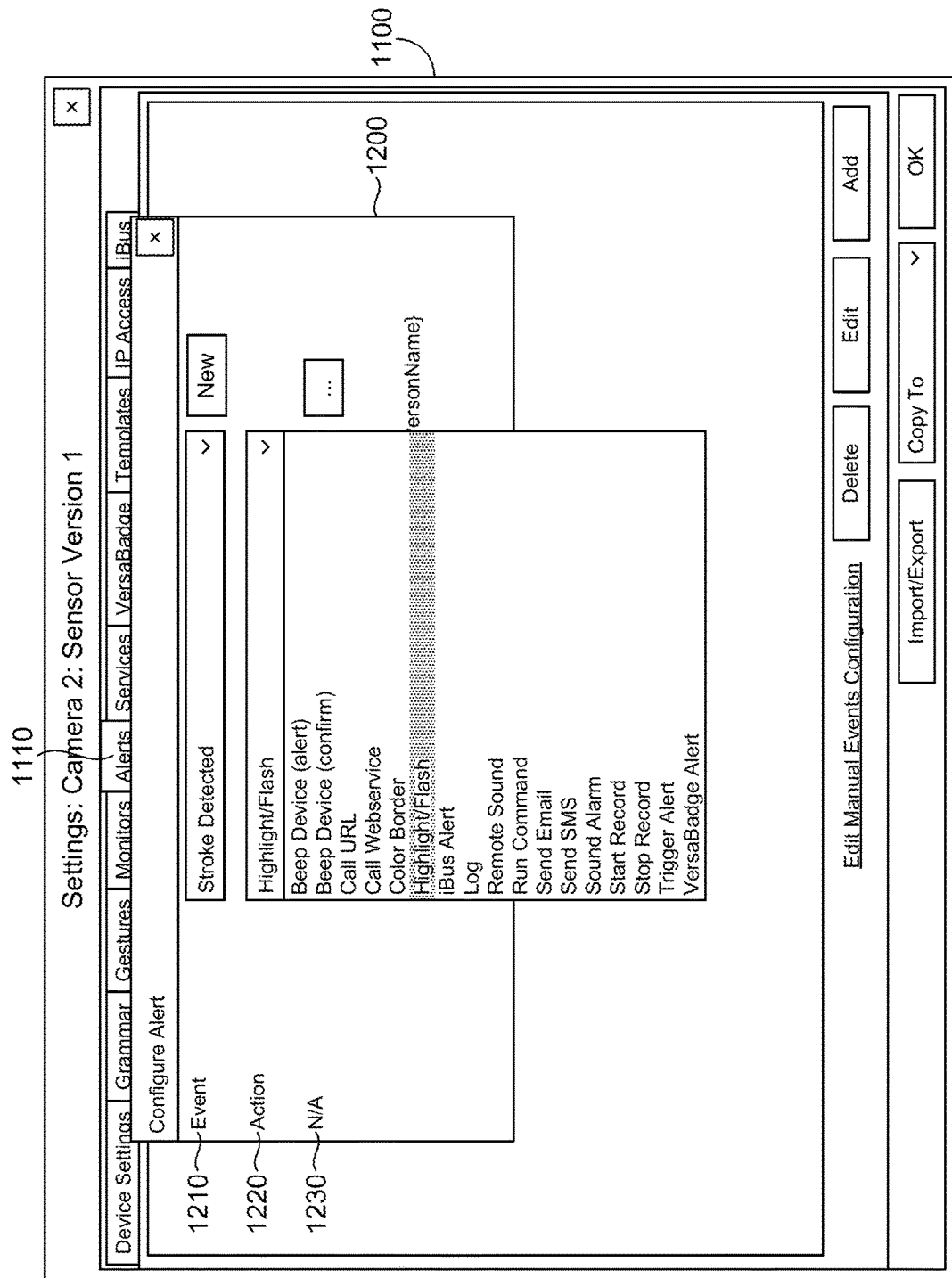
FIG. 13 is an exemplary configuration menu for a stroke detection system.
Figure 14:
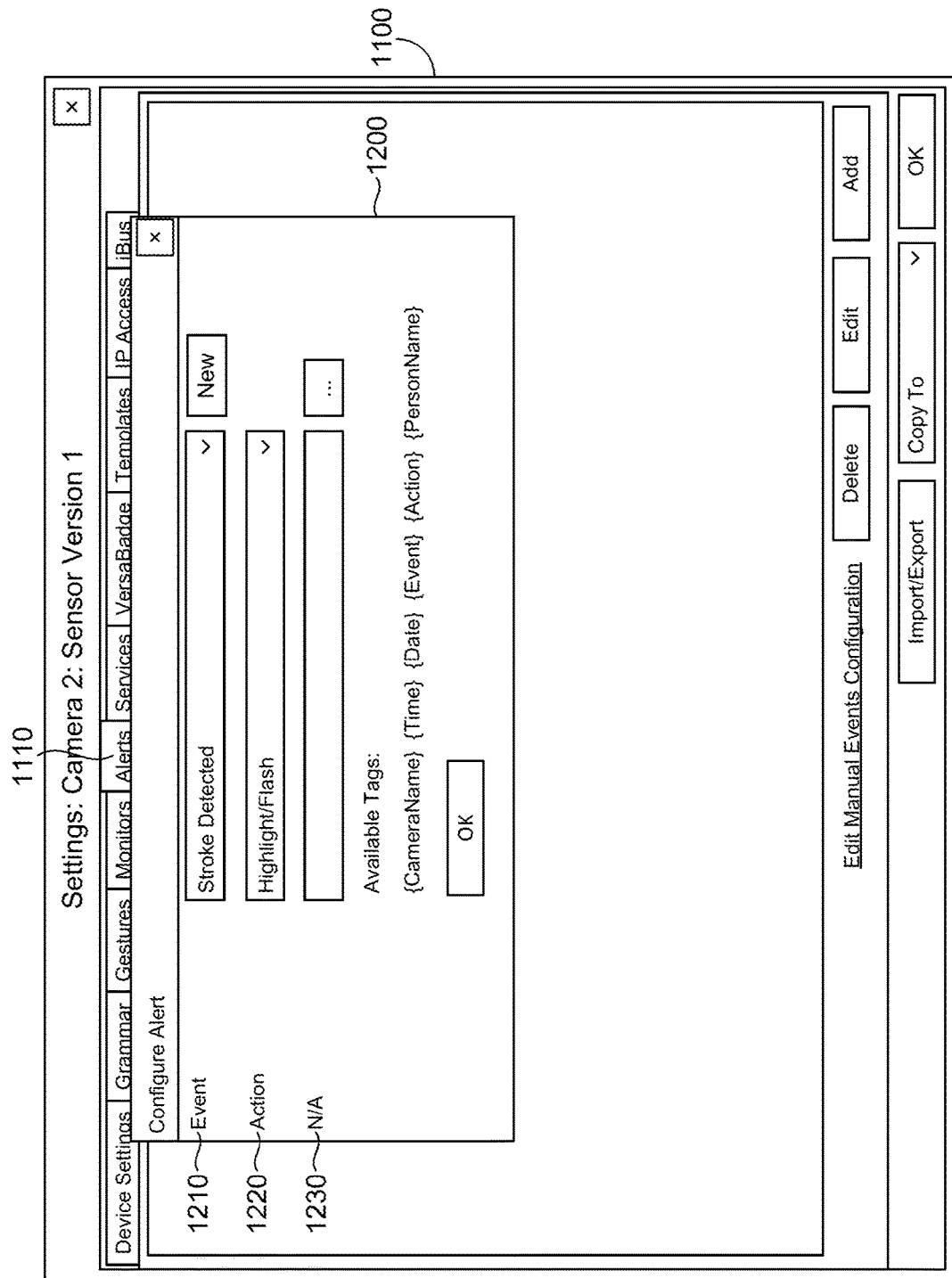
FIG. 14 is an exemplary configuration menu for a stroke detection system.

On selection of an event 1210 in FIG. 12, the user may be able to select an action 1220, as shown in FIG. 13. Several of the options relate to alerts, e.g., to provide different audible signals to the 3D motion sensor 110 and/or computerized monitoring system 130; to add or change a color border to a display of image data; to highlight or flash a display of image data; to log an alert, as in database 160; to send e-mail or SMS; or to provide other alerts. As shown in FIG. 13, the user has elected to highlight/flash a display of image data if event 1210 occurs, e.g., if symptoms of a stroke are detected. As shown in FIG. 14, N/A field 1230 may be blank and/or inactive depending upon the event 1210 and action 1220 selected. In the example shown in FIG. 14, the option to highlight/flash an image display does not require further configuration, and so N/A field 1230 is blank and inactive, in that the user cannot input options for N/A field 1230. However, if the action 1220 was set to send an alert, for example, N/A field 1230 might become active and allow a user to designate a recipient and/or recipient group to whom the alert should be sent. If the user desires to send different kinds of alerts to different recipients or groups of recipients, multiple alerts could be configured, with each alert specifying a different action 1220 (e.g., send e-mail vs. send SMS) and/or a different recipient. As another example, the N/A field 1230 could be used to specify where to log the occurrence of an event, for example, if more than one database 160 is available to the stroke detection system 100, or if data for more than one monitored person is stored in the available database(s).

Figure 15:
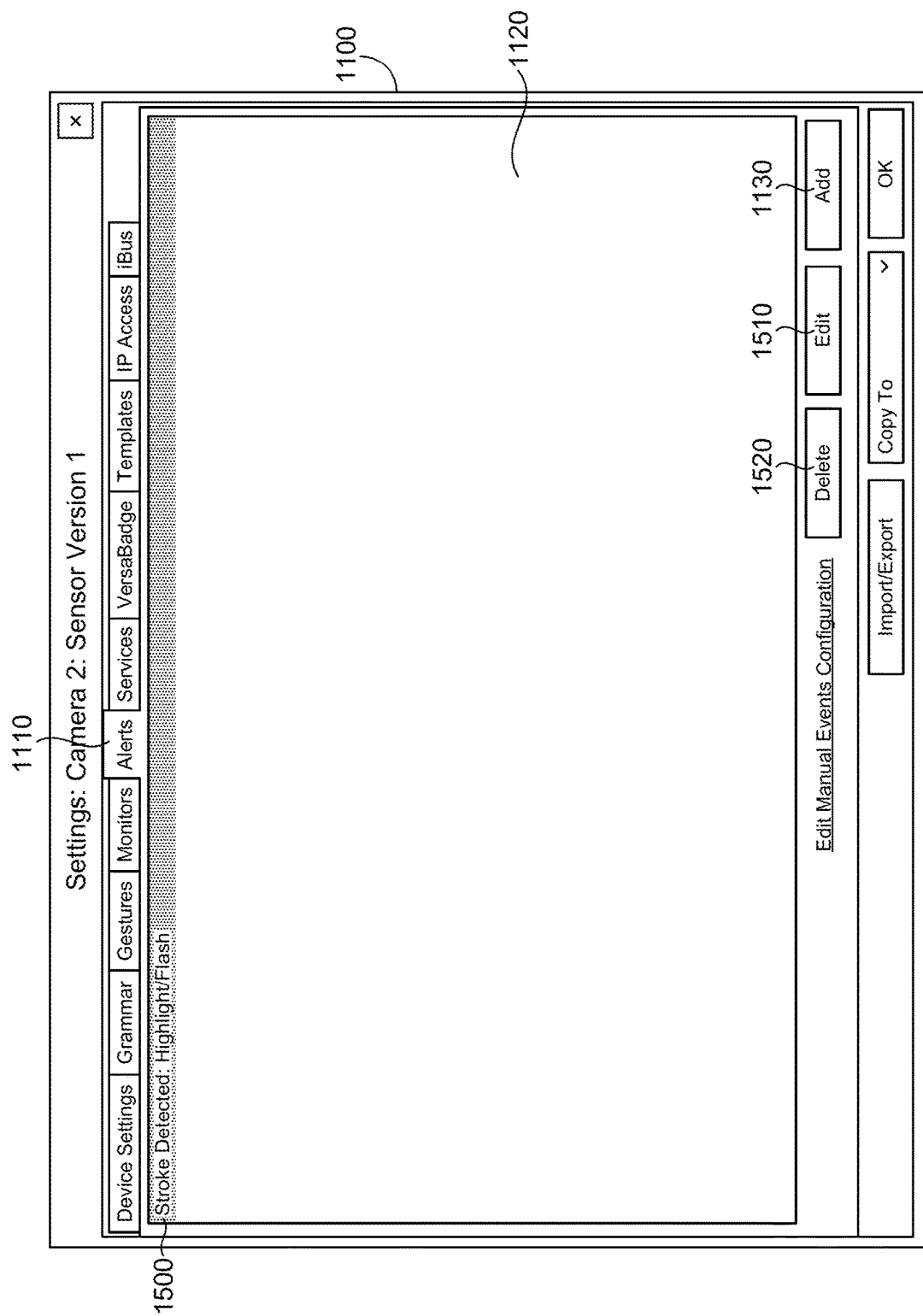
FIG. 15 is an exemplary configuration menu for a stroke detection system.

As shown in FIG. 15, after an alert has been configured, the configuration view 500 may revert to alert tab 1110, now showing a brief description of configured alert 1500 in alerts window 1120. If additional alerts were configured, alerts window 1120 might display a selectable list of configured alerts, including configured alert 1500. Once configured, alerts may be edited or deleted using buttons 1510 or 1520, respectively. Edit button 1510 may re-open the configuration view 500 as shown in FIG. 14, with the drop-down menus open to receive alternate selections.

Figure 16:
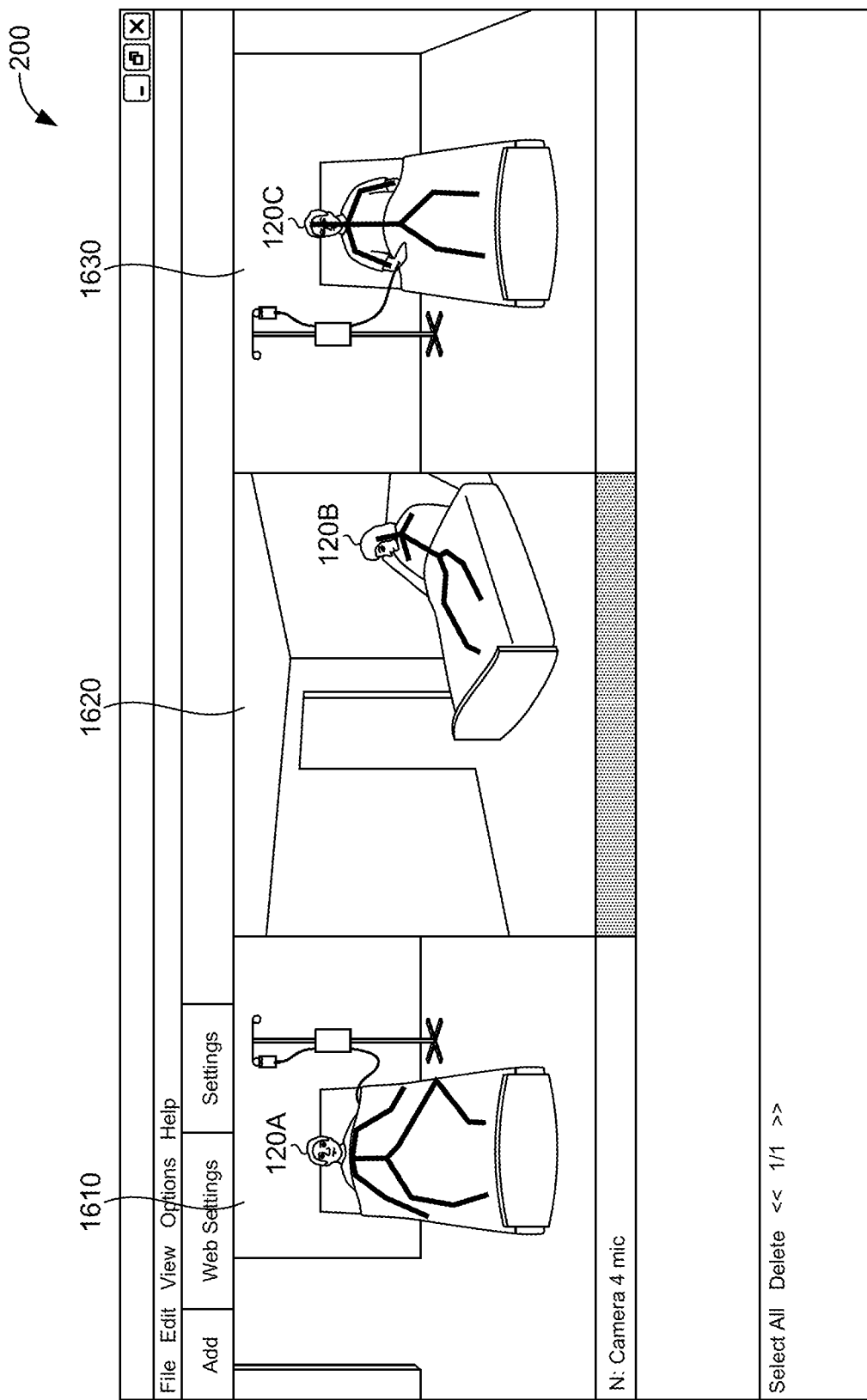
FIG. 16 is an exemplary display for a stroke detection system.

FIG. 16 shows a view of image data from multiple 3D motion sensors 110 monitoring persons 120A, 120B, and 120C, as might appear on a central monitor primary display 200. The configuration window 410 that was shown in FIG. 4 has been closed, providing an unobstructed view of monitored person 120C. Depending upon the configuration for primary display 200, each panel 1610, 1620, and 1630 may display live video, intermittent images (e.g., "still" shots from a video data feed) and/or audio data for monitored person 120A, 120B, and 120C, respectively.

The various computerized systems and processors as described herein may include, individually or collectively, and without limitation, a processing unit, internal system memory, and a suitable system bus for coupling various system components, including database 160, with a control server. Computerized monitoring system 130 and/or central monitoring station 150 may provide control server structure and/or function. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The computerized systems typically include therein, or have access to, a variety of computer-readable media, for instance, database 160. Computer-readable media can be any available media that may be accessed by the computerized system, and includes volatile and nonvolatile media, as well as removable and non-removable media. By way of example, and not limitation, computer-readable media may include computer-storage media and communication media. Computer-readable storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server. Computer-readable storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-readable storage media discussed above, including database 160, provide storage of computer readable instructions, data structures, program modules, and other data for the computerized systems. Computer readable instructions embodied on computer-readable storage media may be accessible by stroke detection system 100 and/or component(s) thereof, and, when executed by a computer processor and/or server, may cause the system to function and/or perform the methods described herein.

The computerized systems may operate in a computer network using logical connections to one or more remote computers. Remote computers may be located at a variety of locations, for example, but not limited to, hospitals and other inpatient settings, veterinary environments, ambulatory settings, medical billing and financial offices, hospital administration settings, home health care environments, payer offices (e.g., insurance companies), home health care agencies, clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers may also be physically located in non-traditional medical care environments so that the entire health care community may be capable of integration on the network. The remote computers may be personal computers, servers, routers, network PCs, peer devices, other common network nodes, or the like, and may include some or all of the elements described above in relation to the control server. The devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the control server may include a modem or other means for establishing communications over the WAN, such as the Internet. In a networked environment, program modules or portions thereof may be stored in the control server, in the database 160, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers may be utilized.

In operation, a user may enter commands and information into the computerized system(s) using input devices, such as a keyboard, a pointing device (commonly referred to as a mouse), a trackball, a touch pad, a 3D Gesture recognition camera or motion sensor. Other input devices may include, without limitation, microphones, satellite dishes, scanners, or the like. In addition to or in lieu of a monitor, the computerized systems may include other peripheral output devices, such as speakers and a printer.

Many other internal components of the computerized system hardware are not shown because such components and their interconnection are well known. Accordingly, additional details concerning the internal construction of the computers that make up the computerized systems are not further disclosed herein.

Methods and systems of embodiments of the present disclosure may be implemented in a WINDOWS or LINUX operating system, operating in conjunction with an Internet-based delivery system, however, one of ordinary skill in the art will recognize that the described methods and systems can be implemented in any operating system suitable for supporting the disclosed processing and communications.

As contemplated by the language above, the methods and systems of embodiments of the present invention may also be implemented on a stand-alone desktop, personal computer, cellular phone, smart phone, tablet computer, PDA, or any other computing device used in a healthcare environment or any of a number of other locations.

From the foregoing, it will be seen that this disclosure is well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A computerized method for detecting stroke symptoms comprising:
    capturing image data including two or more images including a face of a person using at least one 3-dimensional (3D) sensor;
    superimposing at least one axis of a 3-dimensional (3D) axis system at a reference anatomical feature of the face in a portion of the image data including the face of the person; and
    communicating an electronic alert to a remote device in response to detecting an asymmetric change in position of at least one reference point of a plurality of reference points that correspond to anatomical features on the face of the person within the image data relative to the 3D axis system, wherein the detected asymmetric change in position of the at least one reference point represents a change in a degree of asymmetry corresponding to a depth axis in the 3D axis system, and wherein the change in the degree of asymmetry exceeds a threshold change of about 10% or 3 mm in the degree of asymmetry.

2. The computerized method of claim 1, wherein the 3D axis system is a 3D Cartesian coordinate system, and the at least one axis includes an x-axis or y-axis.

3. The computerized method of claim 2, wherein detecting the asymmetric change in position of at least one reference point of a plurality of reference points comprises:
    defining an initial position for the plurality of reference points that correspond to one or more additional anatomical features on the face of the person relative to the x-axis, the y-axis, and the z-axis using at least a portion of the image data;
    tracking the plurality of reference points in the image data;
    computing changes in position of the plurality of reference points relative to the at least one axis of the 3-dimensional (3D) axis system; and
    determining that the asymmetric change in the position of the at least one reference point is consistent with a stroke symptom based on a computed change in position of the at least one reference point is maintained for a minimum number of images included in the image data.

4. The method of claim 1 further comprising communicating the image data to a central monitoring station.

5. The method of claim 4, wherein image data for a plurality of people being monitored are displayed on a primary display at the central monitoring station.

6. The method of claim 5, wherein electronically communicating the electronic alert to a remote device further comprises issuing the electronic alert to the central monitoring station.

7. The method of claim 5, wherein upon the central monitoring station receiving the alert, images of the person for whom the determination of the asymmetric change in facial features was made are displayed on an alert display of the central monitoring station.

8. The method of claim 1, wherein the reference anatomical feature comprises one or more of a nose of the person, an ear of the person, a cheek bone of the person, and an orbital bone about an eye socket of the person.

9. The method of claim 1, wherein the one or more additional anatomical features comprises soft tissue anatomical features.

10. A system for detecting stroke symptoms, the system comprising:
- at least one 3-dimensional (3D) sensor located to provide the at least one 3D sensor with a view of a face of a person to be monitored and including at least one camera;
- one or more processors communicatively coupled to the at least one 3D sensor;
- computer readable storage media storing instructions that when executed by the one or more computer processors cause the one or more processors to:
  - capture a series of images including the face of the person;
  - superimpose at least one axis of a 3-dimensional (3D) axis system at a reference anatomical feature of the face in a portion of the series of images; and
  - broadcast an electronic alert in response to detection of an asymmetric change in position of at least one reference point of a plurality of reference points that correspond to anatomical features on the face of the person within the series of images relative to the 3D axis system, wherein the detected asymmetric change in position of the at least one reference point represents a change in a degree of asymmetry corresponding to a depth axis in the 3D axis system, and wherein the change in the degree of asymmetry exceeds a threshold change of about 10% or 3 mm in the degree of asymmetry.

11. The system of claim 10, wherein the 3D axis system is a 3D Cartesian coordinate system, and the at least one axis includes an x-axis or y-axis.

12. The system of claim 10, wherein the instructions further cause the one or more processors to:
- define an initial position for the plurality of reference points that correspond to one or more additional anatomical features on the face of the person relative to the 3D axis system;
- track the plurality of reference points through the series of images;
- compute changes in position of the plurality of reference points relative to the 3-dimensional (3D) axis system; and
- determining that the asymmetric change in the position of the at least one reference point is consistent with a stroke symptom based on a computed change in position of the at least one reference point is maintained for a minimum number of images included in the series of images.

13. The system of claim 10, wherein the instructions further cause the one or more processors to communicate image data for the series of images to a central monitoring station.

14. The system of claim 13, wherein the broadcast of the electronic alert comprises issuing the electronic alert to the central monitoring station.

15. The system of claim 14, wherein upon receipt of the electronic alert the central monitoring station, the series of images are displayed by the central monitoring station.

16. The system of claim 10, wherein the reference anatomical feature comprises one or more of a nose of the person, an ear of the person, a check bone of the person, or an orbital bone about an eye socket of the person.

17. Non-transitory computer-readable storage media having embodied thereon instructions which, when executed by one or more computer processors, cause the one or more computer processors to:
- capture a series of images including a face of a person using at least one 3-dimensional (3D) sensor;
- superimpose at least one axis of a 3-dimensional (3D) axis system at a reference anatomical feature of the face in a portion of the series of images; and
- broadcast an electronic alert in response to detection of an asymmetric change in position of at least one reference point of a plurality of reference points that correspond to anatomical features on the face of the person within the series of images relative to the 3D axis system, wherein the detected asymmetric change in position of the at least one reference point represents a change in a degree of asymmetry corresponding to a depth axis in the 3D axis system, and wherein the change in the degree of asymmetry exceeds a threshold change of about 10% or 3 mm in the degree of asymmetry.

18. The computer-readable storage media of claim 17, wherein the 3D axis system is a 3D Cartesian coordinate system, and the at least one axis includes an x-axis or y-axis.

19. The computer-readable storage media of claim 17, wherein the instructions further cause the one or more processors to:
- define an initial position for the plurality of reference points that correspond to one or more additional anatomical features on the face of the person relative to the 3D axis system;
- track the plurality of reference points through the series of images;
- compute changes in position of the plurality of reference points relative to the 3-dimensional (3D) axis system; and
- determining that the asymmetric change in the position of the at least one reference point is consistent with a stroke symptom based on a computed change in position of the at least one reference point is maintained for a minimum number of images included in the series of images.

* * * * *